US011919856B2

(12) United States Patent
Smith et al.

(10) Patent No.: US 11,919,856 B2
(45) Date of Patent: Mar. 5, 2024

(54) COMPOUNDS

(71) Applicant: UCL BUSINESS LTD, London (GB)

(72) Inventors: Kate Smith, Brentford (GB); Alexis Denis, Brentford (GB); Nerina Dodic, Brentford (GB); John Liddle, Brentford (GB); David Lomas, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 17/848,156

(22) Filed: Jun. 23, 2022

(65) Prior Publication Data
US 2022/0340525 A1  Oct. 27, 2022

Related U.S. Application Data

(63) Continuation of application No. 17/254,854, filed as application No. PCT/GB2019/051761 on Jun. 21, 2019, now abandoned.

(30) Foreign Application Priority Data

Jun. 22, 2018  (GB) ..................................... 1810290
May 13, 2019  (GB) ..................................... 1906708

(51) Int. Cl.
*C07D 209/34* (2006.01)
(52) U.S. Cl.
CPC .................................. *C07D 209/34* (2013.01)
(58) Field of Classification Search
CPC ..................................................... C07D 209/34
See application file for complete search history.

(56) References Cited

U.S. PATENT DOCUMENTS

| 5,019,587 | A | * | 5/1991 | Von Der Saal | ...... | C07D 401/12 |
| | | | | | | 548/454 |
| 8,436,013 | B2 | | 5/2013 | Liu et al. | | |
| 9,801,637 | B2 | | 10/2017 | Mathis et al. | | |

FOREIGN PATENT DOCUMENTS

| CN | 113801053 A | 12/2021 |
| RU | 2567007 C1 | 10/2015 |
| WO | WO 1994021229 A1 | 9/1994 |
| WO | WO 1998034596 A2 | 8/1998 |

OTHER PUBLICATIONS

Berthelier et al., "Discovery of an Inhibitor of Z-Alpha1 Antitrypsin Polymerization," PLOS One, vol. 10, No. 5, 18 pages, (2015).
Chang et al., "Identification of a 4-mer Peptide Inhibitor that Effectively Blocks the Polymerization of Pathogenic Z [alpha] 1-Antitrypsin," American Journal of Respiratory Cell and Molecular Biology, vol. 35, No. 5, pp. 540-548, (2006).
Huntington et al., "3T1P: Crystal Structure of an Alpha-1-antitrypsin Trimer," RCSB PDB Protein Data Bank, 4 pages, (2011); retrieved from https://www.rcsb.org/structure/3T1P on Jan. 20, 2022.
STNext Database, CAPLUS Accession No. 1990:235173, 6 pages (1990); retrieved on Mar. 17, 2022 from <https://www.stn.org/stn/#/>.
Written Opinion of the International Searching Authority for International Application No. PCT/GB2019/051761 dated Oct. 10, 2019, 6 pages.
Bazzan et al., 2018, "α1-Antitrypsin Polymerizes in Alveolar Macrophages of Smokers With and Without α1-Antitrypsin Deficiency," Chest, 154(3):607-616.
Berge et al., 1977, "Pharmaceutical salts," J. Pharm. Sci., 66(1):1-19.
Chapman et al., 2015, "Intravenous augmentation treatment and lung density in severe α1 antitrypsin deficiency (RAPID): a randomised, double-blind, placebo-controlled trial," Lancet, 386(9991):360-368.
Dafforn et al., 1999, "A kinetic mechanism for the polymerization of alpha1-antitrypsin," J. Biol. Chem., 274(14):9548-9555.
Dickens et al., 2016, "The endoplasmic reticulum remains functionally connected by vesicular transport after its fragmentation in cells expressing Z-α1-antitrypsin," FASEB J., 30(12):4083-4097.
Ekeowa et al., 2010, "Defining the mechanism of polymerization in the serpinopathies," Proc. Natl. Acad. Sci. USA, 107(40):17146-17151.
Elliott et al., 2000, "Topography of a 2.0 A structure of alpha1-antitrypsin reveals targets for rational drug design to prevent conformational disease," Protein Sci., 9(7):1274-1281.
Fregonese et al., 2008, "Alpha-1 antitrypsin Null mutations and severity of emphysema," Respir. Med., 102(6):876-884.
Gooptu et al., 2000, "Inactive conformation of the serpin alpha(1)-antichymotrypsin indicates two-stage insertion of the reactive loop: implications for inhibitory function and conformational disease," Proc. Natl. Acad. Sci. USA, 97(1):67-72.
Guo et al., 2014, "Antisense oligonucleotide treatment ameliorates alpha-1 antitrypsin-related liver disease in mice," J. Clin. Invest., 124(1):251-261 (Epub 2013).
Haq et al., 2013, "Reactive centre loop mutants of α-1-antitrypsin reveal position-specific effects on intermediate formation along the polymerization pathway," Biosci. Rep., 33(3):e00046 (13 pages).
Hidvegi et al., 2010, "An autophagy-enhancing drug promotes degradation of mutant alpha1-antitrypsin Z and reduces hepatic fibrosis," Science, 329(5988):229-232.
International Searching Authority, International Search Report and Written Opinion for International Patent Application No. PCT/GB2019/051761 (Pub No. WO 2019243841) dated Oct. 10, 2019 (10 pages).

(Continued)

*Primary Examiner* — Shawquia Jackson
(74) *Attorney, Agent, or Firm* — JONES DAY

(57) ABSTRACT

The present invention relates to compounds, compositions, combinations and medicaments containing said compounds and processes for their preparation. The invention also relates to the use of said compounds, combinations, compositions and medicaments, for example as modulators of alpha I antitrypsin and treating diseases associated with alpha antitrypsin, particularly liver diseases.

23 Claims, 3 Drawing Sheets
Specification includes a Sequence Listing.

(56) References Cited

OTHER PUBLICATIONS

Irving et al., 2011, "The serpinopathies studying serpin polymerization in vivo," Methods Enzymol., 501:421-466.

Lomas et al., 1992, "The mechanism of Z alpha 1-antitrypsin accumulation in the liver," Nature, 357(6379):605-607.

Lomas et al., 1993, "Effect of the Z mutation on the physical and inhibitory properties of alpha 1-antitrypsin," Biochemistry, 32(2):500-508.

Miranda et al., 2010, "A novel monoclonal antibody to characterize pathogenic polymers in liver disease associated with alpha1-antitrypsin deficiency," Hepatology, 52(3):1078-1088.

Motamedi-Shad et al., 2016, "An antibody that prevents serpin polymerisation acts by inducing a novel allosteric behaviour," Biochem. J., 473(19):3269-3290.

Nettleship et al., 2008, "Methods for protein characterization by mass spectrometry, thermal shift (ThermoFluor) assay, and multiangle or static light scattering," Methods Mol. Biol., 426:299-318.

Ordonez et al., 2013, "Endoplasmic reticulum polymers impair luminal protein mobility and sensitize to cellular stress in alpha1-antitrypsin deficiency," Hepatology, 57(5):2049-2060.

Ordonez et al., 2015, "A single-chain variable fragment intrabody prevents intracellular polymerization of Z α1-antitrypsin while allowing its antiproteinase activity," FASEB J., 29(6):2667-2678.

Tan et al., 2014, "Circulating polymers in α1-antitrypsin deficiency," Eur. Respir. J., 43(5):1501-1504.

Teckman et al., 2004, "Mitochondrial autophagy and injury in the liver in alpha 1-antitrypsin deficiency," Am. J. Physiol. Gastrointest. Liver Physiol., 286(5):G851-G862 (Epub 2003).

Tew et al., 2001, "Probing the equilibrium denaturation of the serpin alpha(1)-antitrypsin with single tryptophan mutants; evidence for structure in the urea unfolded state," J. Mol. Biol., 313(5):1161-1169.

Whisstock et al., 2000, "Conformational changes in serpins: I. The native and cleaved conformations of alpha(1)-antitrypsin," J. Mol. Biol., 295(3):651-665.

Yamasaki et al., 2011, "Molecular basis of α1-antitrypsin deficiency revealed by the structure of a domain-swapped trimer," EMBO Rep., 12(10):1011-1017.

Yusa et al., 2011, "Targeted gene correction of α1-antitrypsin deficiency in induced pluripotent stem cells," Nature, 478(7369):391-394.

Mitchell et al., 2017, "Liver Disease in Alpha-1 Antitrypsin Deficiency: Current Approaches and Future Directions," Curr. Pathobiol. Rep., 5(3):243-252.

Chang, 2012, "Chapter 13: Inhibiting Pathogenic Protein Aggregation: Combinatorial Chemistry in Combating Alpha-1 Antitrypsin Deficiency," in New Strategies in Chemical Synthesis and Catalysis, First Edition, Wiley-VCH Verlag GmbH & Co. KGaA, pp. 299-324.

Parfrey et al., 2004, "Inhibiting polymerization: new therapeutic strategies for Z alpha1-antitrypsin-related emphysema," Am. J. Respir. Cell Mol. Biol., 31(2):133-139.

\* cited by examiner

COMPOUNDS

CROSS-REFERENCE TO RELATED APPLICATIONS

This application is a continuation of U.S. patent application Ser. No. 17/254,854, filed Dec. 21, 2020, which is the U.S. National Phase under 35 USC 371 of, and claims the benefit of and priority to, International Application No. PCT/GB2019/051761, filed Jun. 21, 2019, which claims the benefit of and priority to Great Britain Patent Application No. 1906708.1, filed May 13, 2019, and Great Britain Patent Application No. 1810290.5, filed Jun. 22, 2018, the contents of each of which are incorporated herein by reference in their entireties.

FIELD OF THE INVENTION

The present invention relates to compounds, compositions, combinations and medicaments containing said compounds and processes for their preparation. The invention also relates to the use of said compounds, combinations, compositions and medicaments, for example in the treatment of diseases and conditions associated with alpha 1 antitrypsin.

BACKGROUND OF THE INVENTION

Many human genetic disorders are caused by mutations that impair protein folding and trafficking. The proteins may be produced in normal amounts but because of their impaired folding can lead to problems.

Alpha-1-antitrypsin or aiantitrypsin (A1AT) is a protease inhibitor belonging to the serpin superfamily. It is a protein made in hepatocytes and, and to a lesser extent other cells, and secreted into the blood where it functions to limit enzymatic activity of key proteases, in particular neutrophil elastase. In its absence (such as in alpha-1-antitrypsin deficiency) the activity of key proteases including neutrophil elastase is unchecked resulting in excessive break down of elastin and connective tissues. The most common tissue in which this manifests pathologically is in the lung where the increased degradation of lung connective tissue commonly results in respiratory complications such as emphysema or chronic obstructive pulmonary disease (COPD). More rarely other tissues can also be affected by an A1AT deficiency/dysfunction such as the skin.

In many patients alpha-1-antitrypsin deficiency is caused by mutations including for example an E342K (Glu342Lys) missense mutation herein referred to as the Z mutant (Z-AT). Mutant Z alpha-1-antitrypsin forms polymers which accumulate in cells and can disturb function of the affected tissue. The organ most commonly affected by a build-up of polymer in alpha-1 antitrypsin deficiency is the liver, causing damage to the liver and in severe cases progressing to a requirement for liver transplant. Polymers of A1AT are also found in other tissues including blood, lungs and skin. Polymers have been shown to be pro-inflammatory and may contribute to pathology in tissues where they are found, particularly the lung and the skin.

Current therapy for conditions associated with alpha-1-antitrypsin deficiency is limited to protein replacement therapy with M-AT (wild type alpha 1 antitrypsin protein) derived from human plasma, typically dosed on a weekly basis. While such therapy is effective for lung pathology including emphysema, it has no effect on liver disease caused by the accumulation of polymerized Z-AT in the ER of hepatocytes. For the 10-15% of homozygotes for Z-AT afflicted liver disease including fibrosis, cirrhosis and hepatocellular carcinoma, liver transplantation is the only treatment option available. Furthermore, accumulation of polymerized Z-AT in lung epithelium has a chemoattractant effect on neurophils, which may cause further destruction of connective lung tissue. Thus there is a need for therapeutics and methods that address disease conditions associated with both alpha-1-antitrypsin deficiency as well as toxic accumulation of alpha-1-antitrypsin.

The present inventors have identified compounds which are capable of modulating alpha 1 antitrypsin, particularly the mutant Z-AT form, preventing its polymerization in the liver thus being potentially useful in treating diseases associated with alpha 1 antitrypsin, more particularly with mutant forms of alpha 1 antitrypsin, particularly Z-AT, including diseases of the liver.

The present inventors have, in particular, identified compounds that are capable of binding to $\alpha_1$-antitrypsin in such a way as to prevent polymerisation of the protein and thereby give rise to beneficial therapeutic effects. While $\alpha_1$-antitrypsin proteins have previously been crystallised and their three-dimensional structure studied, the binding site of the compounds identified by the inventors has not previously been identified. As discussed in more detail herein, it is a cryptic binding site formed via interaction between the protein and the present compounds, the specific location and structure of which gives rise to the beneficial inhibition of protein polymerisation. The present inventors have, furthermore, identified specific structural motifs that contribute to the creation of the relevant cryptic binding site and binding of the compounds therein. Thus, the present invention therefore addresses a longstanding need for the provision of compounds that are capable of treating diseases or conditions mediated by $\alpha_1$-antitrypsin polymerisation.

SUMMARY OF THE INVENTION

In a first aspect, the present invention provides a substance for use in a method for treatment of a disease or condition mediated by $\alpha_1$-antitrypsin polymerisation, wherein said substance is: (a) a compound that is capable of inhibiting $\alpha_1$-antitrypsin polymerisation; or (b) a pharmaceutically acceptable solvate, complex, tautomer, isotopically labelled derivative or prodrug thereof. Preferably, the disease or condition is mediated by Z-$\alpha_1$-antitrypsin polymerisation and the compound is capable of inhibiting Z-$\alpha_1$-antitrypsin polymerisation. The substance is typically a small molecule compound, e.g. a compound that has a molecular weight of 1000 Daltons or less.

Preferably, the compound is capable of binding to $\alpha_1$-antitrypsin by inducing formation of a cryptic binding site within the $\alpha_1$-antitrypsin protein structure, said $\alpha_1$-antitrypsin comprising the sequence of SEQ ID NO: 1. For instance, the binding site may be located between β-sheet-A and β-sheet-B of said $\alpha_1$-antitrypsin, wherein: said β-sheet-A comprises the amino acids corresponding to residues 140-144, 111-121, 181-191, 330-340 and 292-299 of SEQ ID NO: 1; and said β-sheet-B comprises the amino acids corresponding to residues 228-231, 236-244, 248-256, 369-376, 381-389, and 49-53 of SEQ ID NO: 1. More preferably, the binding site is located between amino acid strands corresponding to each of: (a) residues 191-194 of SEQ ID NO: 1; (b) residues 288-293 of SEQ ID NO: 1; (c) residues 371-374 of SEQ ID NO: 1; (d) residues 249-253 of SEQ ID NO: 1; and (e) residues 240-243 of SEQ ID NO: 1; and optionally also (f) residues 338-341 of SEQ ID NO: 1.

The binding site may comprise one or more of W194, Y244, L291, P289, F252, K290, I293, L338, I340, F372 and M374 of SEQ ID NO: 1.

Preferably, the $K_D$ of the compound to M-$\alpha_1$-antitrypsin is less than about 250 nM, said M-$\alpha_1$-antitrypsin comprising the sequence of SEQ ID NO: 2. Preferably, the $K_D$ of the compound to Z-$\alpha_1$-antitrypsin is less than about 25 nM, said Z-$\alpha_1$-antitrypsin comprising the sequence of SEQ ID NO: 3. Preferably, the $K_D$ of the compound to Z-$\alpha_1$-antitrypsin is at least ten times lower than the $K_D$ of the compound to M-$\alpha_1$-antitrypsin, said M-$\alpha_1$-antitrypsin comprising the sequence of SEQ ID NO: 2 and said Z-$\alpha_1$-antitrypsin comprising the sequence of SEQ ID NO: 3.

The compound may comprise a tetravalent moiety of formula (IA)

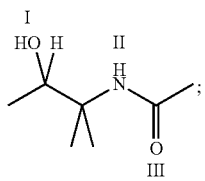

(IA)

wherein the compound is capable of binding to $\alpha_1$-antitrypsin comprising the sequence of SEQ ID NO: 1 by hydrogen bond formation between: (i) hydroxyl group I and L291 of SEQ ID NO: 1; (ii) NH group II and P289 of SEQ ID NO: 1; and (iii) carbonyl group III and Y244 of SEQ ID NO: 1. For instance, the compound may comprise a divalent moiety of formula (IB)

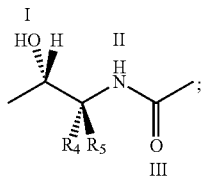

(IB)

wherein: the compound is capable of binding to $\alpha_1$-antitrypsin comprising the sequence of SEQ ID NO: 1 by hydrogen bond formation between: (i) hydroxyl group I and L291 of SEQ ID NO: 1; (ii) NH group II and P289 of SEQ ID NO: 1; and (iii) carbonyl group III and Y244 of SEQ ID NO: 1; $R_4$ is selected from hydrogen, $C_{1-5}$ alkyl, $C_{2-5}$ alkenyl, $C_{2-5}$ alkynyl and $C_{1-4}$ alkoxy; and $R_5$ is selected from hydrogen, $C_{1-5}$ alkyl, $C_{2-5}$ alkenyl, $C_{2-5}$ alkynyl and $C_{1-4}$ alkoxy. Optionally $R_5$ is hydrogen. Optionally $R_4$ is $C_{2-4}$ alkyl, $C_{2-4}$ alkenyl, $C_{2-4}$ alkynyl or $C_{1-3}$ alkoxy. Optionally $R_4$ is n-propyl.

More specifically, the compound may comprise a monovalent moiety of formula (IC)

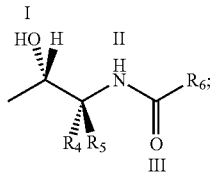

(IC)

wherein: the compound is capable of binding to $\alpha_1$-antitrypsin comprising the sequence of SEQ ID NO: 1 by hydrogen bond formation between: (i) hydroxyl group I and L291 of SEQ ID NO: 1; (ii) NH group II and P289 of SEQ ID NO: 1; and (iii) carbonyl group III and Y244 of SEQ ID NO: 1; $R_4$ and $R_5$ are as defined above; and $R_6$ is a substituted or unsubstituted aryl or heteroaryl group capable of stacking with the side chain of W194 of SEQ ID NO: 1. Optionally, $R_6$ is a substituted or unsubstituted 4-oxindolyl group. For instance, optionally $R_6$ is a group of formula $R_6'$

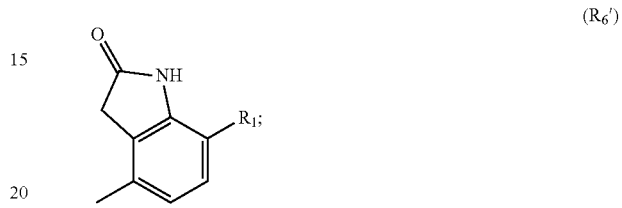

($R_6'$)

wherein $R_1$ is selected from the group consisting of H, F, $CH_3$, $CH_2CH_3$, $CH_2CH_2CH_3$, $CH(CH_3)_2$, $NH_2$, $NHCH_3$, $N(CH_3)_2$, OH, Cl, Br and I. Optionally $R_1$ is selected from the group consisting of H, F, $CH_3$, $NH_2$, OH and Cl. For instance optionally $R_1$ is selected from the group consisting of H and F.

More specifically still, the compound may have the formula (ID)

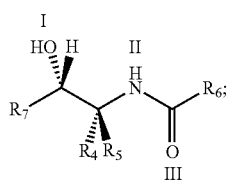

(ID)

wherein: the compound is capable of binding to $\alpha_1$-antitrypsin comprising the sequence of SEQ ID NO: 1 by hydrogen bond formation between: (i) hydroxyl group I and L291 of SEQ ID NO: 1; (ii) NH group II and P289 of SEQ ID NO: 1; and (iii) carbonyl group III and Y244 of SEQ ID NO: 1; $R_4$ and $R_5$ are as defined above; $R_6$ is as defined above; and $R_7$ is a substituted or unsubstituted aryl or heteroaryl group.

Optionally $R_7$ is a substituted or unsubstituted phenyl group. For instance, optionally $R_7$ is a group of formula $R_7'$

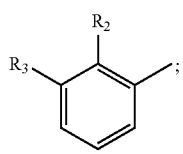

($R_7'$)

wherein: $R_2$ is selected from the group consisting of $CH_3$, Cl, $CH_2CH_3$, $CH_2CH_2CH_3$, $CH(CH_3)_2$, $NH_2$, $NHCH_3$, $N(CH_3)_2$, OH, SH, CN, F, Br and I; and $R_3$ is selected from the group consisting of F, Cl, CN, $CH_3$, $CH_2CH_3$, $CH_2CH_2CH_3$, $CH(CH_3)_2$, $NH_2$, $NHCH_3$, $N(CH_3)_2$, OH, Br, I and SH. Optionally, $R_2$ is selected from the group consisting of $CH_3$, Cl, $NH_2$, OH, SH, CN and F; and $R_3$ is selected from the group consisting of F, Cl, CN, CH₃, NH₂, OH and SH. For instance, optionally R₂ is selected from the group consisting of CH₃ and Cl; and R₃ is selected from the group consisting of F, Cl and CN.

For instance, the compound may have the formula (I)

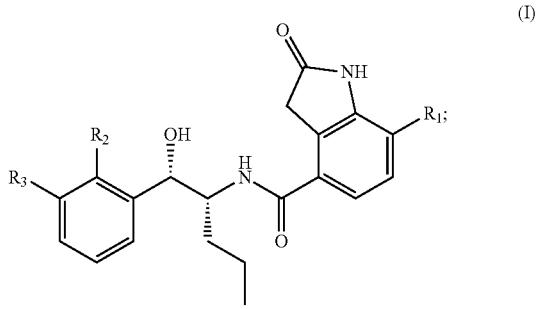

wherein: $R_1$ is selected from the group consisting of H, F, $CH_3$, $CH_2CH_3$, $CH_2CH_2CH_3$, $CH(CH_3)_2$, $NH_2$, $NHCH_3$, $N(CH_3)_2$, OH, Cl, Br and I; $R_2$ is selected from the group consisting of $CH_3$, Cl, $CH_2CH_3$, $CH_2CH_2CH_3$, $CH(CH_3)_2$, $NH_2$, $NHCH_3$, $N(CH_3)_2$, OH, SH, CN, F, Br and I; and $R_3$ is selected from the group consisting of F, Cl, CN, $CH_3$, $CH_2CH_3$, $CH_2CH_2CH_3$, $CH(CH_3)_2$, $NH_2$, $NHCH_3$, $N(CH_3)_2$, OH, Br, I and SH.

Optionally in formula (I): $R_1$ is selected from the group consisting of H, F, $CH_3$, $NH_2$, OH and Cl; $R_2$ is selected from the group consisting of $CH_3$, Cl, $NH_2$, OH, SH, CN and F; and $R_3$ is selected from the group consisting of F, Cl, CN, $CH_3$, $NH_2$, OH and SH. For example, optionally: $R_1$ is selected from the group consisting of H and F; $R_2$ is selected from the group consisting of $CH_3$ and Cl; and $R_3$ is selected from the group consisting of F, Cl and CN. For instance, optionally: $R_1$ is H, $R_2$ is $CH_3$ and $R_3$ is F; or $R_1$ is H, $R_2$ is $CH_3$ and $R_3$ is Cl; or $R_1$ is F, $R_2$ is Cl and $R_3$ is CN; or $R_1$ is F, $R_2$ is Cl and $R_3$ is F.

The present invention also provides a substance as defined above. Still further, the present invention provides a method for identifying a drug candidate compound, the method comprising: contacting the drug candidate compound with $\alpha_1$-antitrypsin comprising the sequence of SEQ ID NO: 1 to form a complex between the drug candidate compound and said $\alpha_1$-antitrypsin; resolving the structure of the complex; and determining whether, in the complex, the drug candidate compound is present in a binding site as defined above.

In still further aspects, the present invention provides the following embodiments [1] to [11].

[1] a compound that: (a) has the formula (I):

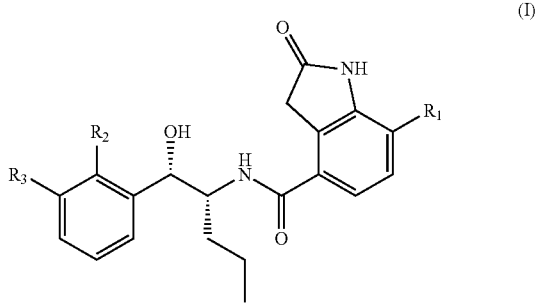

wherein: $R_1$ is H, $R_2$ is $CH_3$ and $R_3$ is F; or $R_1$ is H, $R_2$ is $CH_3$ and $R_3$ is Cl; or $R_1$ is F, $R_2$ is Cl and $R_3$ is CN; or $R_1$ is F, $R_2$ is Cl and $R_3$ is F; or (b) is a pharmaceutically acceptable solvate, complex, tautomer, isotopically labeled derivative or prodrug thereof.

[2] A compound as defined in [1] for use in therapy.

[3] A compound as defined in [1] for use in the treatment of a disease or condition mediated by alpha 1 antitrypsin.

[4] A pharmaceutical composition comprising a compound as defined in [1] and one or more of pharmaceutically acceptable carriers, diluents and excipients.

[5] A method of treating a disease or condition mediated by alpha 1 antitrypsin in a subject comprising administering a therapeutically effective amount of a compound as defined in [1].

[6] Use of a compound as defined in [1], in the manufacture of a medicament for use in treating a disease or condition mediated by alpha 1 antitrypsin.

[7] A combination comprising a compound as defined in [1], and at least one further therapeutic agent.

[8] A combination comprising a compound as defined in [1] and at least one further therapeutic agent for use in therapy, particularly for treating a disease or condition mediated by alpha 1 antitrypsin.

[9] A combination comprising a compound as defined in [1] and at least one further therapeutic agent for use in treating a disease or condition mediated by alpha 1 antitrypsin.

[10] A method of treating a disease or condition mediated by alpha 1 antitrypsin comprising administering to a human in need thereof a therapeutically effective amount of a combination comprising a compound as defined in [1], and at least one further therapeutic agent.

[11] Use of a combination comprising a compound as defined in [1] and at least one further therapeutic agent in the manufacture of a medicament for treating a disease or condition mediated by alpha 1 antitrypsin.

DETAILED DESCRIPTION OF THE INVENTION

Definitions

Figure 1:
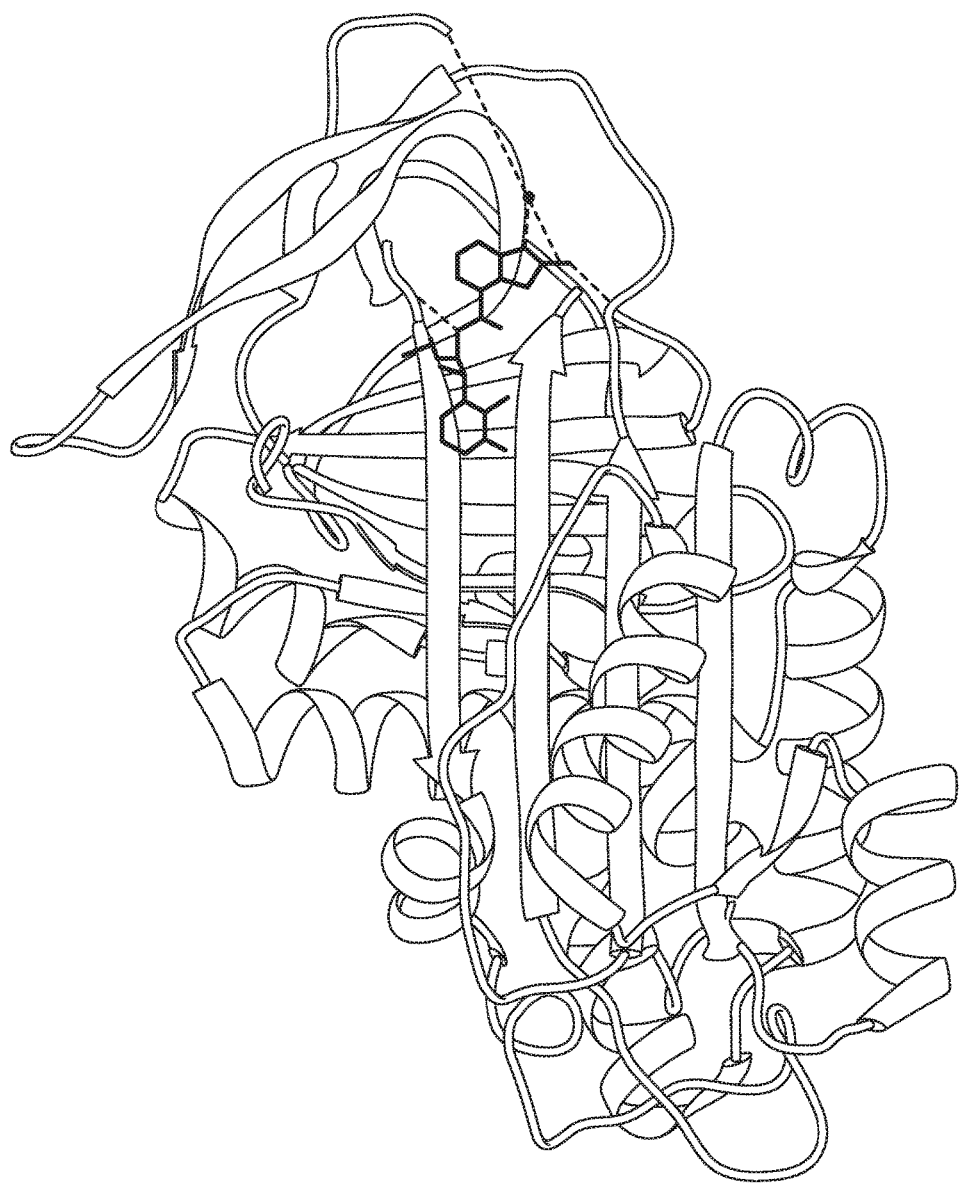
FIG. 1 is a representative image of the crystallised complex formed between a representative compound of the present invention and an $\alpha_1$-antitrypsin protein, as described in more detail in Example 2.

As used herein, an alkyl group is a straight or branched saturated hydrocarbon radical. In one example an alkyl group contains 1 to 5 carbon atoms. Examples of alkyl groups include methyl, ethyl, n-propyl, iso-propyl, n-butyl, sec-butyl, tert-butyl, n-pentyl, isopentyl and neopentyl.

As used herein, an alkenyl group is a straight or branched hydrocarbon radical that contains one or more (e.g. one) carbon carbon double bonds. In one example an alkenyl group contains 2 to 5 carbon atoms.

As used herein, an alkenyl group is a straight or branched hydrocarbon radical that contains one or more (e.g. one) carbon carbon triple bonds. In one example an alkynyl group contains 2 to 5 carbon atoms.

As used herein, an alkoxy group (e.g., a $C_{1-4}$ alkoxy group) is a group of formula —OR in which R is an alkyl (e.g. a $C_{1-4}$ alkyl) group.

As used herein, an alkylthiol group (e.g., a $C_{1-4}$ alkylthiol group) is a group of formula —SR in which R is an alkyl (e.g. a $C_{1-4}$ alkyl) group.

As used herein, an aryl group is typically a $C_{6-14}$ mono-carbocyclic, aromatic ring or poly-carbocyclic ring system, wherein at least one of the rings therein is aromatic. Preferably such a group is a $C_{6-10}$ mono-carbocyclic, aromatic ring or bi-carbocyclic ring system, wherein at least one of the rings therein is aromatic. Examples include phenyl, naphthyl, and indanyl. Unless expressly indicated otherwise, valency may be located on any atom of any ring of the aryl group.

As used herein, a heteroaryl group is typically a 5 to 14 ring atom-containing monocyclic, aromatic ring or polycyclic ring system, wherein at least one of the rings therein is aromatic. The heteroaryl group contains at least one (e.g., 1, 2, 3 or 4) ring heteroatom selected from O, S, N (e.g., forming at least one ring O, $S(O)_x$ (in which x is 0, 1 or 2), N, NH or $N^+O^-$ moiety), with the other ring atoms being carbon atoms. Preferably such a group contains 5 to 10 ring atoms. Unless expressly indicated otherwise, valency may be located on any atom of any ring of the heteroaryl group.

Examples of monocyclic heteroaryl groups include thienyl, furyl, pyrrolyl, imidazolyl, thiazolyl, isothiazolyl, pyrazolyl, oxazolyl, isoxazolyl, triazolyl, thiadiazolyl, oxadiazolyl, pyridinyl, pyridazinyl, pyrimidinyl, pyrazinyl, triazinyl and tetrazolyl groups.

Examples of polycyclic heteroaryl groups include oxindolyl, benzothienyl, benzofuranyl, benzimidazolyl, benzothiazolyl, benzisothiazolyl, benzoxazolyl, benzisoxazolyl, benztriazolyl, indolyl, isoindolyl and indazolyl groups. Oxindolyl includes 2-oxindolyl (i.e. a monovalent group derived from 2-oxindole, also known as 2-Indolinone) and 3-oxindolyl (i.e., a monovalent group derived from 3-oxindole, also known as 3-Indolinone).

In an aryl group or heteroaryl group, at least one (e.g. 1, 2 or 3) carbon ring atom may be substituted by a carbonyl group (i.e. —C(O)—). For instance, a benzoxazolyl may optionally comprise —C(O)— in place of carbon at its 2-position, thereby giving rise to a monovalent heteroaryl group derived from benzoxazolone.

Unless otherwise specified, an aryl or heteroaryl group is typically unsubstituted. However, where such a group is indicated to be unsubstituted or substituted, one or more hydrogen atoms are optionally replaced by deuterium atoms, halogen atoms or hydroxyl, thiol (—SH), nitro, sulfonic acid, nitrile (—CN), amino (e.g., —$NR_2$ where each R is independently selected from H and $C_{1-5}$ alkyl), alkyl (e.g., $C_{1-5}$ alkyl), deuterarated alkyl (e.g., $C_{1-5}$ deuterated alkyl), alkenyl (e.g., $C_{2-5}$ alkenyl), alkynyl (e.g., $C_{2-5}$ alkynyl), haloalkyl (e.g., $C_{1-5}$ haloalkyl), haloalkenyl (e.g., $C_{2-5}$ haloalkenyl), alkoxy (e.g., $C_{1-4}$ alkoxy), alkylthio (e.g., $C_{1-4}$ alkylthio), alkylsulfonyl (e.g., $C_{1-4}$ alkylsulfonyl), haloalkoxy (e.g., $C_{1-4}$ haloalkoxy), haloalkylthio (e.g., $C_{1-4}$ haloalkylthio), haloalkylsulfonyl (e.g., $C_{1-4}$ haloalkylsulfonyl), cycloalkyl (e.g., $C_{3-5}$ cycloalkyl) or heterocycloalkyl (e.g., $C_{3-5}$ heterocycloalkyl).

Preferred such substituents are deuterium atoms, fluorine atoms, chlorine atoms, or hydroxyl, nitro, nitrile (—CN), —$NR_2$ (where each R is independently selected from H and methyl), $C_{1-5}$ alkyl, —$CD_3$, $C_{2-3}$ alkenyl, $C_{2-3}$ alkynyl, $CF_3$, $CHF_2$, $CH_2CF_3$, $C_2F_5$, $CF=CF_2$, $C_{1-3}$ alkoxy, $C_{1-3}$ alkylthio, $C_{1-3}$ alkylsulfonyl, $OCF_3$, $SCF_3$, $SO_2CF_3$, cyclopropyl, cyclobutyl, oxetanyl and azetidinyl.

Preferably, a substituted aryl or heteroaryl group has from 1 to 5 substituents, more preferably 1 to 3 substituents and most preferably 1 or 2 substituents. Preferably a substituted aryl or heteroaryl group carries not more than 2 nitro substituents and not more than 2 sulfonic acid substituents.

As used herein, halogen atoms are typically F, Cl, Br or I atoms, preferably F or Cl atoms.

For the avoidance of doubt, the terms $\alpha_1$-antitrypsin, alpha-1-antitrypsin, alpha 1 antitrypsin, etc., are used interchangeably herein.

Unless otherwise specified, all references to organic groups containing one more hydrogen atoms also include their partially or fully deuterated counterparts. For instance, references herein to alkyl groups embrace alkyl groups consisting of carbon and hydrogen atoms, alkyl groups containing carbon atoms and a mixture of hydrogen and deuterium atoms, and fully deuterated alkyl groups. Preferably, however, such organic groups are not partially or fully deuterated except where expressly indicated.

General Information Regarding Compounds of the Invention, Pharmaceutical Compositions Comprising Such Compounds, and Combination Therapies As used herein, "a compound of the invention" includes compounds that are capable of inhibiting $\alpha_1$-antitrypsin polymerisation and all solvates, complexes, tautomers, polymorphs, isotope labelled derivatives, stereoisomers and optical isomers of such compounds.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The compounds of the present invention may be in the form of a salt.

Typically, the salts of the present invention are pharmaceutically acceptable salts. Salts encompassed within the term "pharmaceutically acceptable salts" refer to non-toxic salts of the compounds of this invention. For a review on suitable salts see Berge et al, J. Pharm. Sci. 1977, 66, 1-19.

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compound of the present invention may exist in solvated and unsolvated forms. As used herein, the term "solvate" refers to a complex of variable stoichiometry formed by a solute (in this invention, a compound of the invention and a solvent). Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water. The present invention includes all such solvates.

The compounds of the invention may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process.

Polymorphs can be distinguished by various physical characteristics known in the art such as x-ray diffraction patterns, solubility and melting point.

It is also noted that the compounds of the invention may form tautomers. It is understood that all tautomers and mixtures of tautomers of the compounds of the present invention are included within the scope of the compounds of the present invention.

The invention also includes isotopically-labelled compounds, which are identical to the compounds of the invention, but for the fact that one or more atoms are replaced by an atom having an atomic mass or mass number different from the atomic mass or mass number most commonly found in nature. Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Isotopically-labelled compounds of the present invention can generally be prepared by conventional techniques known to those skilled in the art or by processes analogous to those described in the accompanying Examples and Preparations using an appropriate isotopically-labelled reagents in place of the non-labelled reagent previously employed.

In one embodiment the compound of the present invention is one of:

| Example number | structure | name |
|---|---|---|
| 1 | 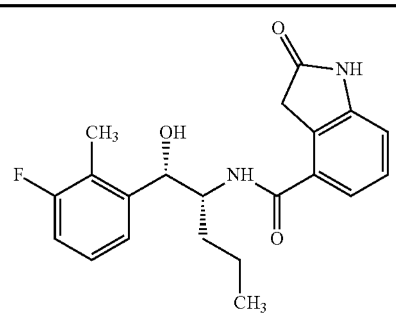 | N-((1S,2R)-1-(3-fluoro-2-methylphenyl)-1-hydroxypentan-2-yl)-2-oxoindoline-4-carboxamide |
| 2 | 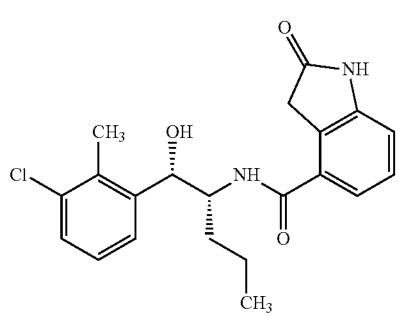 [SMILES: CCC[C@@H](NC(=O)c1cccc2c1CC(=O)N2)[C@@H](O)c1cccc(Cl)c1C] | N-((1S,2R)-1-(3-chloro-2-methylphenyl)-1-hydroxypentan-2-yl)-2-oxoindoline-4-carboxamide |

-continued

| Example number | structure | name |
|---|---|---|
| 3 | 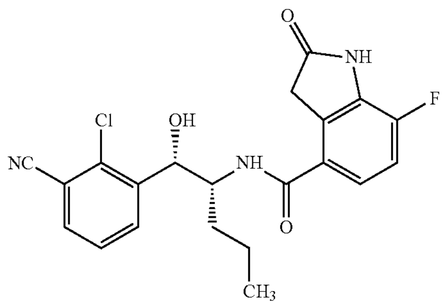 [SMILES: CCC[C@@H](NC(=O)c1ccc(F)c2c1CC(=O)N2)[C@@H](O)c1cccc(C#N)c1Cl] | N-((1S,2R)-1-(2-chloro-3-cyanophenyl)-1-hydroxypentan-2-yl)-7-fluoro-2-oxoindoline-4-carboxamide |
| 4 | 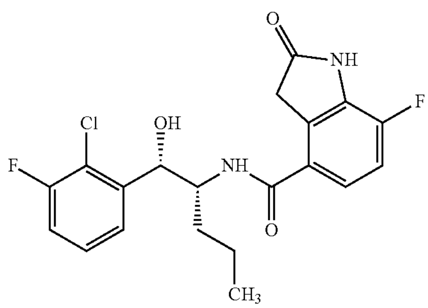 [SMILES: CCC[C@@H](NC(=O)c1ccc(F)c2c1CC(=O)N2)[C@@H](O)c1cccc(F)c1Cl] | N-((1S,2R)-1-(2-chloro-3-fluorophenyl)-1-hydroxypentan-2-yl)-7-fluoro-2-oxoindoline-4-carboxamide |

While it is possible that, for use in therapy, the compound of the invention may be administered as the raw chemical, it is possible to present the compound of the invention as the active ingredient in a pharmaceutical composition. Such compositions can be prepared in a manner well known in the pharmaceutical art and comprise at least one active compound. Accordingly, the invention further provides pharmaceutical compositions comprising a compound of the invention and one or more pharmaceutically acceptable excipients. The excipient(s) must be acceptable in the sense of being compatible with the other ingredients of the composition and not deleterious to the recipient thereof. In accordance with another aspect of the invention there is also provided a process for the preparation of a pharmaceutical composition including the agent, with one or more pharmaceutically acceptable excipients. The pharmaceutical composition can be for use in the treatment and/or prophylaxis of any of the conditions described herein.

Generally, the compound of the invention is administered in a pharmaceutically effective amount. The amount of the compound actually administered will typically be determined by a physician, in the light of the relevant circumstances, including the condition to be treated, the chosen route of administration, the actual compound—administered, the age, weight, and response of the individual patient, the severity of the patient's symptoms, and the like.

Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert excipient such as ethanol, glycerol, water and the like. Powders are prepared by reducing the compound to a suitable fine size and mixing with a similarly prepared pharmaceutical excipient such as an edible carbohydrate, as, for example, starch or mannitol. Flavouring, preservative, dispersing and colouring agent can also be present.

Capsules are made by preparing a powder mixture, as described above, and filling formed gelatin sheaths. Excipients including glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, excipients including suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, suspensions, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like. The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions drops, gels or dry powders.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation.

Intranasal compositions may permit the compound(s) of the invention to be delivered to all areas of the nasal cavities (the target tissue) and further, may permit the compound(s) of the invention to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition.

Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of the invention and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

In one embodiment, a composition suitable for inhaled administration may be incorporated into a plurality of sealed dose containers provided on medicament pack(s) mounted inside a suitable inhalation device. The containers may be rupturable, peelable, or otherwise openable one-at-a-time and the doses of the dry powder composition administered by inhalation on a mouthpiece of the inhalation device, as known in the art. The medicament pack may take a number of different forms, for instance a disk-shape or an elongate strip.

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece.

Pressurised aerosol compositions suitable for inhalation can be either a suspension or a solution and may contain a compound of the invention or a pharmaceutically acceptable salt thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional composition excipients well known in the art such as surfactants e.g. oleic acid, lecithin or an oligo-lactic acid or derivative thereof e.g. as described in WO 94/21229 and WO 98/34596 (Minnesota Mining and Manufacturing Company) and co-solvents e.g. ethanol. Pressurised compositions will generally be retained in a canister (e.g. an aluminium canister) closed with a valve (e.g. a metering valve) and fitted into an actuator provided with a mouthpiece.

Pharmaceutical compositions adapted for vaginal administration may be presented as pessaries, tampons, creams, gels, pastes, foams or spray formulations.

Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

Suitably, the amount of the compound of the invention administered according to the present invention will be an amount selected from 0.01 mg to 5 g per day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

Specific, and strictly non-limiting, examples of prodrugs within the meaning of the present invention include derivatives of compounds of formulae (IA), (IB), (IC), (ID) and (I) in which the hydroxyl moiety is replaced by a reactive moiety that is capable of degrading in vivo (e.g., by hydrolysis) to yield the hydroxyl moiety. For avoidance of doubt, the hydroxyl moiety of formulae (IA), (IB), (IC) and (ID) is that indicated by the label "I" in the chemical formulae, and the hydroxyl moiety of formula (I) is that attached to the carbon atom that is between the phenyl ring and the propyl side group of the compound. Similarly, the present invention includes derivatives of compounds of formula (II) in which Z is a reactive moiety that is capable of degrading in vivo (e.g., by hydrolysis) to yield a hydroxyl moiety. Strictly non-limiting, and merely representative, examples of such reactive moieties include moieties of formula $OR_z$ in which $R_z$ has the formula $PO_3H_2$, $CO(CH_2)$, $NH_2$ and $PO_3H(CH_2)_n$—$NH_2$ (where n is integer, e.g. of from 2 to 5). As those skilled in the art would readily appreciate, a wealth of other reactive moieties could also be used. In a compound containing a plurality of hydroxyl groups, it is of course possible for some or all of the said hydroxyl groups to replace by such reactive moieties.

The compounds of the invention may be employed alone or in combination with other therapeutic agents. The compounds of the invention and the other pharmaceutically active agent(s) may be administered together or separately and, when administered separately, administration may occur simultaneously or sequentially, in any order. by any convenient route in separate or combined pharmaceutical compositions.

The amounts of the compound(s) of the invention and the other pharmaceutically active agent(s) and the relative timings of administration will be selected in order to achieve the desired combined therapeutic effect. The compounds of the present invention and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and visa versa. Such sequential administration may be close in time (e.g. simultaneously) or remote in time. Furthermore, it does not matter if the compounds are administered in the same dosage form, e.g. one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited, For example, one agent may be administered once a day, and the other agent may be administered 2 or 3 times a day, or one agent may be administered once a week, and the other agent may be administered once a day and the like.

It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of the invention is used in combination with a second therapeutic agent active against the same disease, condition or disorder, the dose of each compound may differ from that when the compound is used alone. Appropriate doses will be readily appreciated by those skilled in the art.

In one embodiment the mammal in the methods and uses of the present invention is a human.

Detailed Description of Compounds of the Present Invention

The compound of the present invention is a compound that is capable of inhibiting $\alpha_1$-antitrypsin polymerisation. Typically, the compound is capable of inhibiting Z-$\alpha_1$-antitrypsin polymerisation.

The compound is typically a small molecule compound. As used herein, a small molecule compound typically has a molecular weight of 2000 Daltons or less, more usually 1000 Daltons or less and preferably 800 Daltons or less. More preferably the molecular weight is 600 or less and most preferably 500 or less. For instance, the small molecule drug may have a molecular weight of from 250 to 800, such as from 300 to 600.

In one aspect of the present invention, the compound that is capable of inhibiting $\alpha_1$-antitrypsin polymerisation is a compound of the general formula (II):

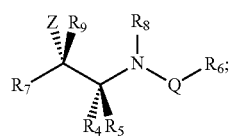

(II)

wherein:
$R_4$, $R_5$, $R_6$ and $R_7$ are as defined elsewhere herein (e.g., with respect to general formula (ID));
$R_8$ is hydrogen, deuterium, alkyl (e.g., $C_{1-5}$ alkyl) or deuterated alkyl (e.g., $C_{1-5}$ deuterated alkyl);
$R_9$ is hydrogen, deuterium, alkyl (e.g., $C_{1-5}$ alkyl) or deuterated alkyl (e.g., $C_{1-5}$ deuterated alkyl);
Z is OH, F, —NHCHO, —CH$_2$F, —CHF$_2$ or CF$_3$; and
Q is —C(=O)—, —C(=S)—, —C(=NOH)—, —C(=NNH$_2$)— or —S(O)$_2$—.

Examples of preferred groups $R_4$, $R_5$, $R_6$ and $R_7$ are as defined elsewhere herein.

Preferred groups $R_8$ are hydrogen, deuterium, and $C_{1-2}$ optionally deuterated alkyl. More preferably $R_8$ is hydrogen, methyl or ethyl, more preferably still hydrogen or methyl and most preferably hydrogen.

Preferred groups $R_9$ are hydrogen, deuterium, and $C_{1-2}$ optionally deuterated alkyl. More preferably $R_9$ is hydrogen, methyl or ethyl, more preferably still hydrogen or methyl and most preferably hydrogen.

Z is preferably OH or F, most preferably OH.

Q is preferably —C(=O)—, —C(=S)— or —S(O)$_2$—, more preferably —C(=O)— or —C(=S)—, and most preferably —C(=O)—.

In preferred embodiments, the compound of general formula (II) is a compound of general formula (ID), and more preferably still a compound of general formula (I), as further defined elsewhere herein.

Binding of the Compound to $\alpha_1$-Antitrypsin

The compound of the present invention is capable of binding to $\alpha_1$-antitrypsin. Typically, the compound is capable of binding to $\alpha_1$-antitrypsin by via a cryptic binding site within the $\alpha_1$-antitrypsin protein structure. A cryptic binding site as defined herein refers to a binding site that is absent, occluded, or only transiently accessed in the unbound protein, but present when the compound is bound to the protein; for instance, the cryptic binding site may come into existence as a consequence of contacting the protein with the compound, and/or a previously only transiently accessed protein configuration featuring the binding site may become stabilized by the presence of the protein.

By "$\alpha_1$-antitrypsin" in the expression "the compound is capable of binding to $\alpha_1$-antitrypsin" is meant a protein that comprises the sequence of SEQ ID NO: 1, namely

X$_1$DPQGDAAQKTDTSHHDQDHPTFNKITPNLAEFAFSLYRQLAHQSNSTNI

FFSPVSIATAFAMLSLGTKADTHDEILEGLNFNLTEIPEAQIHEGFQELL

X$_2$TLNQPDSQLQLTTGNGLFLSEGLKLVDKFLEDVKKLYHSEAFTVNFGDT

EEAKKQINDYVEKGTQGKIVDLVKELDRDTVFALVNYIFFKGKWERPFEVK

DTEEEDFHVDQX$_3$TTVKVPMMKRLGMFNIQHX$_4$KKLSSWVLLMKYLGNATA

IFFLPDEGKLQHLENELTHDIITKFLENEDRRSASLHLPKLSITGTYDLKS

-continued

VLGQLGITKVFSNGADLSGVTEEAPLKLSKAVHKAVLTIDX$_5$KGTEAAGAM

FLEAIPMSIPPEVKFNKPFVFLMIX$_6$QNTKSPLFMGKVVNPTQK wherein $X_1$ is T or E, $X_2$ is R or H, $X_3$ is A or V, $X_4$ is C or S, $X_5$ is E or K, and $X_6$ is D or E.

For the avoidance of doubt, a compound is a compound of the invention if it is capable of binding to any such protein, i.e. any single protein that comprises the sequence of SEQ ID NO: 1 (i.e., it is not essential that the compound must bind to all possible variants embraced by SEQ ID NO: 1, and nor does such binding preclude the possibility that the compound may also bind to other proteins, such as those containing amino acid sequences that differ from SEQ ID NO: 1).

Furthermore, also for the avoidance of doubt, all residue numbers attributed to specific amino acids in the $\alpha_1$-antitrypsin protein, for instance in relation to definition of the binding site of the compounds of the present invention, are counted from the N-terminus of the sequence of SEQ ID NO: 1, i.e. $X_1$ is counted as residue 1, the adjacent D as residue 2, the adjacent P as residue 3, the adjacent Q as residue 4, the adjacent G as residue 5, and so on. This numbering applies also when the protein contains additional amino acids at the N-terminus with respect to SEQ ID NO: 1, i.e. any such additional "flanking" amino acids do not change the numbering convention, with $X_1$ still being counted as residue 1, D as residue 2, P as residue 3, Q as residue 4, G as residue 5, and so on. Thus, the numbering is always counted only with reference to the amino acids of SEQ ID NO: 1 and excludes any additional amino acid residues present, for instance in any signal peptide or affinity tag and/or any additional amino acids provided by an expression vector used in the synthesis of the protein. Consequently in any relevant protein, $X_1$ is amino acid 1, $X_4$ is amino acid 232, $X_5$ is amino acid 342, and so on.

The most common allele of wild-type M-AT is the M1V allele (estimated at 44-49% of total). In the M1V allele, $X_1$ is E, $X_2$ is R, $X_3$ is V, $X_4$ is C, $X_5$ is E and $X_6$ is E. The full human M1V protein further comprises a signal peptide at the N-terminus having the sequence MPSSVSWGILLLAGLC-CLVPVSLA. Thus, the full sequence of the human M1V protein corresponds to the sequence of SEQ ID NO: 2, namely

MPSSVSWGILLLAGLCCLVPVSLAEDPQGDAAQKTDTSHHDQDHPTFNKIT

PNLAEFAFSLYRQLAHQSNSTNIFFSPVSIATAFAMLSLGTKADTHDEILE

GLNFNLTEIPEAQIHEGFQELLRTLNQPDSQLQLTTGNGLFLSEGLKLVDK

FLEDVKKLYHSEAFTVNFGDTEEAKKQINDYVEKGTQGKIVDLVKELDRDT

VFALVNYIFFKGKWERPFEVKDTEEEDFHVDQVTTVKVPMMKRLGMFNIQH

CKKLSSWVLLMKYLGNATAIFFLPDEGKLQHLENELTHDIITKFLENEDRR

SASLHLPKLSITGTYDLKSVLGQLGITKVFSNGADLSGVTEEAPLKLSKAV

HKAVLTIDEKGTEAAGAMFLEAIPMSIPPEVKFNKPFVFLMIEQNTKSPLF

MGKVVNPTQK.

The Z-$\alpha_1$-antitrypsin mutant differs from the M1V allele in that $X_5$ is K rather than E (i.e. the mutation is defined as E342K) and $X_3$ (213) is A. Thus, the full sequence of Z-A1AT corresponds to the sequence of SEQ ID NO: 3, namely

MPSSVSWGILLLAGLCCLVPVSLAEDPQGDAAQKTDTSHHDQDHPTFNKIT

PNLAEFAFSLYRQLAHQSNSTNIFFSPVSIATAFAMLSLGTKADTHDEILE

GLNFNLTEIPEAQIHEGFQELLRTLNQPDSQLQLTTGNGLFLSEGLKLVDK

FLEDVKKLYHSEAFTVNFGDTEEAKKQINDYVEKGTQGKIVDLVKELDRDT

VFALVNYIFFKGKWERPFEVKDTEEEDFHVDQATTVKVPMMKRLGMFNIQH

CKKLSSWVLLMKYLGNATAIFFLPDEGKLQHLENELTHDIITKFLENEDRR

SASLHLPKLSITGTYDLKSVLGQLGITKVFSNGADLSGVTEEAPLKLSKAV

HKAVLTIDKKGTEAAGAMFLEAIPMSIPPEVKFNKPFVFLMIEQNTKSPLF

MGKVVNPTQK.

For ease of handling (e.g. in generating crystals of $\alpha_1$-antitrypsin protein and/or generating complexes of $\alpha_1$-antitrypsin protein bound to a compound of the invention), it may be desirable to mutate cysteine 232 of the protein to a serine, i.e. to effect the mutation C232S. This is a conservative mutation and is not located at a position directly associated with the compound binding site. SEQ ID NO:1 embraces both proteins in view of its variable amino acid residue $X_4$.

In a preferred embodiment, the compound is capable of binding to a protein comprising SEQ ID NO: 1 in which $X_1$ is E, $X_2$ is R, $X_3$ is A, $X_4$ is C, $X_5$ is K and $X_6$ is E, i.e. the sequence has 100% sequence identity to the corresponding portion of Z-$\alpha_1$-antitrypsin.

In another exemplary embodiment, the protein may be a sequence that comprises SEQ ID NO: 1 and which additionally comprises an affinity tag (e.g. a hexahistidine affinity tag) and/or amino acids provided by an expression vector. For instance, such a protein may be one expressed in *E. coli*. The full sequence of one such exemplary protein is that of SEQ ID NO: 4, namely

MRGSHHHHHHTDPQGDAAQKTDTSHHDQDHPTFNKITPNLAEFAFSLYRQL

AHQSNSTNIFFSPVSIATAFAMLSLGTKADTHDEILEGLNFNLTEIPEAQI

HEGFQELLRTLNQPDSQLQLTTGNGLFLSEGLKLVDKFLEDVKKLYHSEAF

TVNFGDTEEAKKQINDYVEKGTQGKIVDLVKELDRDTVFALVNYIFFKGKW

ERPFEVKDTEEEDFHVDQVTTVKVPMMKRLGMFNIQHSKKLSSWVLLMKYL

GNATAIFFLPDEGKLQHLENELTHDIITKFLENEDRRSASLHLPKLSITGT

YDLKSVLGQLGITKVFSNGADLSGVTEEAPLKLSKAVHKAVLTIDEKGTEA

AGAMFLEAIPMSIPPEVKFNKPFVFLMIEQNTKSPLFMGKVVNPTQK.

This protein, which is used in Example 2 herein, comprises N-terminal sequence MRGSHHHHHHT having a hexahistidine affinity tag and amino acids provided by an expression vector used in synthesis, and in which $X_1$ is T. This protein further comprises a serine at position 232 (i.e. $X_4$ is S) to assist ease of handling. This protein further comprises glutamate at position 342 (i.e., $X_5$ is E).

An important finding of the present invention is that the subject compounds are capable of specific binding to the $\alpha_1$-antitrypsin protein in a part of the protein that has not previously been demonstrated to be a site for drug binding (and still less one that, upon formation of compound-protein binding, is capable of inhibiting protein polymerisation).

More particularly, the said binding site is preferably located between β-sheet-A and β-sheet-B of said $\alpha_1$-antitrypsin. Said β-sheet-A comprises the amino acids corresponding to one or more of: (i) residues 140-144; (ii)

residues 111-121; (iii) residues 181-191; (iv) residues 330-340; and (v) residues 292-299 of SEQ ID NO: 1. Preferably said β-sheet-A comprises the amino acids corresponding to two or more of, more preferably three or more, more preferably still four or more, and most preferably all five, of (i) to (v). Said β-sheet-B comprises the amino acids corresponding to one or more of: (i') residues 228-231; (ii') residues 236-244; (iii') residues 248-256; (iv') residues 369-376; (v') residues 381-389; and (vi') residues 49-53 of SEQ ID NO: 1. Preferably said β-sheet-B comprises the amino acids corresponding to two or more of, more preferably three or more, more preferably still four or more, more preferably still five or more, and most preferably all six, of (i') to (vi').

Thus, preferably the binding site is located between β-sheet-A and β-sheet-B of said $\alpha_1$-antitrypsin, wherein: said β-sheet-A comprises the amino acids corresponding to residues 140-144, 111-121, 181-191, 330-340 and 292-299 of SEQ ID NO: 1; and said (3-sheet-B comprises the amino acids corresponding to residues 228-231, 236-244, 248-256, 369-376, 381-389, and 49-53 of SEQ ID NO: 1.

By "located between β-sheet-A and β-sheet-B" is meant that, when the compound is bound to the $\alpha_1$-antitrypsin, at least part (e.g. substantially all or all) of the compound is accommodated in physical space between said β-sheet-A and said β-sheet-B. As will be readily appreciated by those skilled in the art, confirmation of the location of the binding site of the compound on the protein can be provided by methods well known in the art, such as by using routine crystallographic techniques (see, for instance, Example 2 herein).

More specifically still, the binding site is more preferably located between amino acid strands corresponding to three or more of: (a) residues 191-194 of SEQ ID NO: 1; (b) residues 288-293 of SEQ ID NO: 1; (c) residues 371-374 of SEQ ID NO: 1; (d) residues 249-253 of SEQ ID NO: 1; and (e) residues 240-243 of SEQ ID NO: 1. It is particularly preferred that the binding site is located between amino acid strands corresponding to four or more, and most preferably each of: (a) residues 191-194 of SEQ ID NO: 1; (b) residues 288-293 of SEQ ID NO: 1; (c) residues 371-374 of SEQ ID NO: 1; (d) residues 249-253 of SEQ ID NO: 1; and (e) residues 240-243 of SEQ ID NO: 1. It is additionally preferable that the binding site is also located between amino acid strands corresponding to (f) residues 338-341 of SEQ ID NO: 1. By "amino acid strand" is meant a plurality of amino acids residues in the protein as numbered herein, e.g. an amino acid strand corresponding residues 191-194 of SEQ ID NO: 1 refers to amino acids 191, 192, 193 and 194 of SEQ ID NO: 1. By "located between" the said amino acid strands is meant that, when the compound is bound to the oi-antitrypsin, at least part (e.g. substantially all or all) of the compound is accommodated in physical space between the respective amino acid strands.

In an exemplary aspect, the binding site comprises one or more of W194, Y244, L291, P289, F252, K290, I293, L338, I340, F372 and M374 of SEQ ID NO: 1. In this exemplary aspect, the binding site preferably comprises three or more, more preferably five or more, more preferably still seven or more, and more preferably nine or more of W194, Y244, L291, P289, F252, K290, I293, L338, I340, F372 and M374 of SEQ ID NO: 1. The binding site may, for instance, comprise 1, 2, 3, 4, 5, 6, 7, 8, 9, 10 or all 11 of W194, Y244, L291, P289, F252, K290, I293, L338, I340, F372 and M374 of SEQ ID NO: 1. Particularly preferred amino acids associated with the binding site are W194, Y244, L291 and P289 and thus preferably the binding site comprises at least W194, Y244, L291 and P289. As further described herein, the compound may optimally be capable of forming non-covalent bonds (including but not limited to hydrogen bonds) with the functional groups of the relevant amino acid residues of the protein.

Preferably the $K_D$ of the compound to M-$\alpha_1$-antitrypsin is less than about 250 nM, said M-$\alpha_1$-antitrypsin comprising the sequence of SEQ ID NO: 2 and/or the $K_D$ of the compound to Z-$\alpha_1$-antitrypsin is less than about 25 nM, said Z-$\alpha_1$-antitrypsin comprising the sequence of SEQ ID NO: 3. Preferably the $K_D$ of the compound to Z-$\alpha_1$-antitrypsin is at least ten times lower than the $K_D$ of the compound to M-$\alpha_1$-antitrypsin, said M-$\alpha_1$-antitrypsin comprising the sequence of SEQ ID NO: 2 and said Z-$\alpha_1$-antitrypsin comprising the sequence of SEQ ID NO: 3. Methods for measuring $K_D$ are well known in the art and any such method can be used. One exemplary such method is described in Example 2. All references herein to $K_D$ are as determined at room temperature (e.g. at 20° C.).

Preferred Structural Elements Contributing to Protein Binding

In an exemplary aspect of the present disclosure, the compound comprises a β-hydroxyamide moiety, i.e. a moiety of formula —C(OH)(X)—CX$_2$—NH—C(O)—, where each X independently represents a substituent (for instance, any specific substituent as defined elsewhere herein).

Importantly, it has been found that such a β-hydroxyamide structural motif substantially contributes to the ability of the present compounds to bind to $\alpha_1$-antitrypsin at the present binding site. In particular, such a moiety may provide for binding to $\alpha_1$-antitrypsin comprising the sequence of SEQ ID NO: 1 by hydrogen bond formation between: (i) the β-hydroxyl group and L291 of SEQ ID NO: 1; (ii) the NH of the carboxamide group and P289 of SEQ ID NO: 1; and (iii) the carbonyl of the carboxamide group and Y244 of SEQ ID NO: 1.

Accordingly, it is preferred that the compound comprises a tetravalent moiety of formula (IA)

wherein the compound is capable of binding to $\alpha_1$-antitrypsin comprising the sequence of SEQ ID NO: 1 by hydrogen bond formation between: (i) hydroxyl group I and L291 of a SEQ ID NO: 1; (ii) NH group II and P289 of SEQ ID NO: 1; and (iii) carbonyl group III and Y244 of SEQ ID NO: 1.

By tetravalent is meant that the moiety of formula (IA) contains four points of bonding, i.e. at the positions 1, 2, 3 and 4 indicated below:

More preferably the compound comprises a divalent moiety of formula (IB)

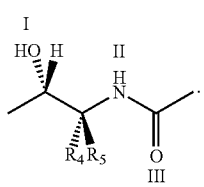
(IB)

By divalent is meant that the moiety of formula (IB) contains two points of bonding, i.e. at the positions 1 and 2 below

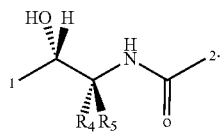

In formula (IB), as in formula (IA), typically the compound is capable of binding to $\alpha_1$-antitrypsin by hydrogen bond formation between: (i) hydroxyl group I and L291 of SEQ ID NO: 1; (ii) NH group II and P289 of SEQ ID NO: 1; and (iii) carbonyl group III and Y244 of SEQ ID NO: 1.

$R_4$ and $R_5$ can be the same or different from one another. They are independently selected from hydrogen, $C_{1-5}$ alkyl, $C_{2-5}$ alkenyl, $C_{2-5}$ alkynyl and $C_{1-4}$ alkoxy.

$R_5$ is preferably hydrogen, methyl, ethyl, ethenyl, ethynyl or methoxy. More preferably $R_5$ is hydrogen, methyl or ethyl. Most preferably $R_5$ is hydrogen.

$R_4$ is preferably $C_{2-4}$ alkyl, $C_{2-4}$ alkenyl, $C_{2-4}$ alkynyl or $C_{1-3}$ alkoxy. More preferably $R_4$ is n-propyl, —CH=CH—CH$_3$, —C—C=CH$_2$ or ethoxy. Most preferably $R_4$ is n-propyl.

A particularly preferred combination of $R_5$ and $R_4$ is when $R_5$ is hydrogen and $R_4$ is n-propyl. The presence of a single n-propyl substituent at the carbon α to the carboxamide has been found to be particularly beneficial for enabling the compound to bind to $\alpha_1$-antitrypsin at the relevant binding site.

More preferably still, the compound comprises a monovalent moiety of formula (IC)

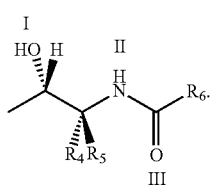
(IC)

By monovalent is meant that the moiety of formula (IC) contains one point of bonding, i.e. at the position 1 below

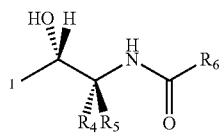

In formula (IC), as in formulae (IA) and (IB), typically the compound is capable of binding to $\alpha_1$-antitrypsin by hydrogen bond formation between: (i) hydroxyl group I and L291 of SEQ ID NO: 1; (ii) NH group II and P289 of SEQ ID NO: 1; and (iii) carbonyl group III and Y244 of SEQ ID NO: 1. $R_4$ and $R_5$ are as defined with reference to formula (IB). $R_6$ is a substituted or unsubstituted aryl or heteroaryl group. Typically, $R_6$ is capable of stacking with the side chain of W194 of SEQ ID NO: 1 when the compound is bound to said $\alpha_1$-antitrypsin.

$R_6$ is preferably substituted or unsubstituted and is: (a) a $C_{6-10}$ aryl group; or (b) a heteroaryl group that contains 5 to 10 ring atoms. More preferably $R_6$ is substituted or unsubstituted and is: (a) a bicarbocyclic aromatic group; or (b) a bicyclic heteroaryl group.

When $R_6$ is an aryl group, particularly preferred groups include naphthyl and indanyl (in both cases substituted or unsubstituted and in both cases wherein optionally one carbon ring atom may be substituted by a carbonyl group), most preferably indanyl (optionally wherein one carbon ring atom may be substituted by a carbonyl group).

When $R_6$ is a heteroaryl group, preferred groups include oxindolyl (e.g., 2-oxindolyl or 3-oxindolyl), benzothienyl, benzofuranyl, benzimidazolyl, benzothiazolyl, benzisothiazolyl, benzoxazolyl, benzisoxazolyl, benzotriazolyl, indolyl, isoindolyl and indazolyl (in all cases substituted or unsubstituted and in all cases wherein optionally one carbon ring atom may be substituted by a carbonyl group) and more preferred groups include oxindolyl (e.g., 2-oxindolyl or 3-oxindolyl), benzothienyl, benzofuranyl, benzimidazolyl, benzothiazolyl, benzoxazolyl and indolyl (in all cases substituted or unsubstituted and in all cases wherein optionally one carbon ring atom may be substituted by a carbonyl group).

For any aryl or heteroaryl group in which one carbon ring atom is substituted by a carbonyl group, the resulting ring entity is —C(O)—. Where the "parent" carbon ring atom forms a double bond to an adjacent ring atom, the substitution of that carbon ring atom to —C(O)— is accompanied by saturation of the said adjacent ring atom, e.g. by addition of a hydrogen atom thereto or an optional substituent as defined herein.

Particularly preferred $R_6$ groups are substituted or unsubstituted bicyclic aryl and heteroaryl groups comprising a six-membered ring fused to a five-membered ring (i.e. containing 9 ring atoms). Of such $R_6$ groups, preferably the ring atom of the five-membered ring that is not adjacent to either of the ring atoms shared by the five-membered ring and the six-membered ring is a carbon atom bearing a carbonyl group, i.e. it is —C(O)—. For instance, preferred $R_6$ groups include the following 6-1 to 6-12:

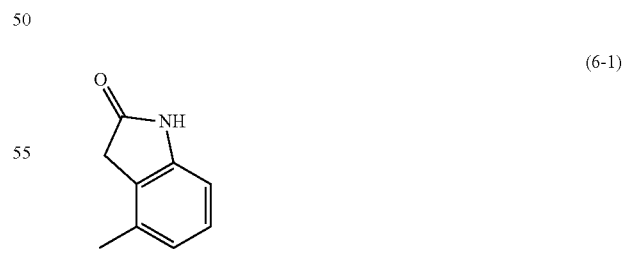
(6-1)

(6-2)

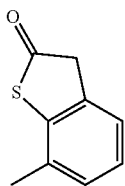 (6-3)

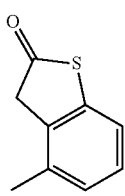 (6-4)

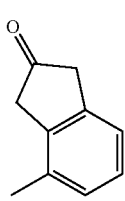 (6-5)

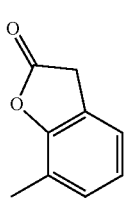 (6-6)

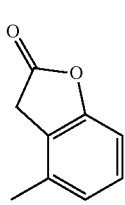 (6-7)

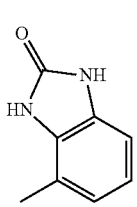 (6-8)

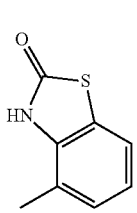 (6-9)

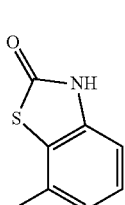 (6-10)

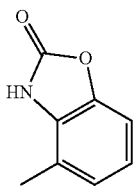 (6-11)

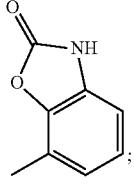 (6-12)

in which one or more H-groups bound to ring atoms (preferably carbon ring atoms) may be replaced by substituents.

More preferably still, $R_6$ is a substituted or unsubstituted 4-oxindolyl group (i.e. a 4-(2-oxindolyl) group), which is group 6-1 above.

Preferably the $R_6$ group is unsubstituted or substituted with 1 to 4 substituents, e.g. 1 or 2 substituents. More preferably the $R_6$ group is unsubstituted or substituted with 1 or 2 substituents. Most preferably the $R_6$ group is unsubstituted or substituted with 1 substituent.

Optional substituents for $R_6$ include those defined in the "Definitions" section herein. Particularly preferred substituents for $R_6$ include halogen atoms, $C_{1-5}$ alkyl, $-NR_2$ (where each R is independently selected from H and $C_{1-5}$ alkyl), and hydroxyl. Still more particularly preferred substituents include F, $CH_3$, $CH_2CH_3$, $CH_2CH_2CH_3$, $CH(CH_3)_2$, $NH_2$, $NHCH_3$, $N(CH_3)_2$, OH, Cl, Br and I and still more preferred substituents are F, $CH_3$, $NH_2$, OH and Cl. Most preferred substitutes are F and Cl (e.g. F).

In an exemplary aspect, $R_6$ is a group of formula $R_6'$

 (R$_6'$)

wherein $R_1$ is selected from the group consisting of H, F, $CH_3$, $CH_2CH_3$, $CH_2CH_2CH_3$, $CH(CH_3)_2$, $NH_2$, $NHCH_3$, $N(CH_3)_2$, OH, Cl, Br and I. In the formula $R_6'$, $R_1$ is more preferably selected from the group consisting of H, F, $CH_3$, $NH_2$, OH and Cl and still more preferably selected from the group consisting of H and F.

It is particularly preferred that the compound has the formula (ID)

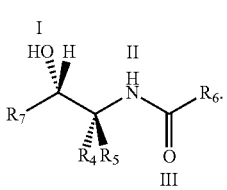 (ID)

In formula (ID), as in formulae (IA), (IB) and (IC), typically the compound is capable of binding to $\alpha_1$-antitrypsin by hydrogen bond formation between: (i) hydroxyl group I and L291 of SEQ ID NO: 1; (ii) NH group II and P289 of SEQ ID NO: 1; and (iii) carbonyl group III and Y244 of SEQ ID NO: 1. $R_4$ and $R_5$ are as defined with reference to formula (IB). $R_6$ is as defined with reference to formula (IC).

$R_7$ in formula (ID) is a substituted or unsubstituted aryl or heteroaryl group. Preferably $R_7$ is a substituted or unsubstituted phenyl, pyridinyl, pyridazinyl, pyrimidinyl pyrazinyl or triazinyl group. More preferably $R_7$ is a substituted or unsubstituted phenyl group.

$R_7$ is preferably substituted by 1, 2, 3, 4 or 5 substituents, more preferably 1, 2 or 3 substituents and most preferably 2 substituents. Optional substituents for $R_7$ include those defined in the "Definitions" section herein. Particularly preferred $R_7$ substituents include halogen atoms and $C_{1-5}$ alkyl, $-NR_2$ (where each R is independently selected from H and $C_{1-5}$ alkyl), hydroxyl, —SH and —CN groups.

A particularly preferred $R_7$ is a phenyl group substituted with 1, 2, 3, 4 or 5 (preferably at least 2) substituents. Preferably such a phenyl group comprises at least a meta-substituent and an ortho-substituent, i.e. it is of formula $R_7''$

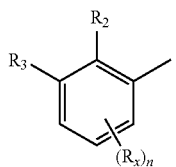

wherein $R_2$ and $R_3$ are substituents, each $R_x$ is an independently selected substituent and n is an integer of from 0 to 3. More preferably such a phenyl group has the formula $R_7'$

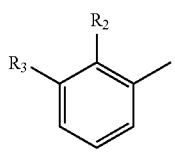

Preferably in $R_7'$ and $R_7''$, each of $R_2$, $R_3$ and any $R_x$ is independently selected from halogen atoms and $C_{1-5}$ alkyl, $-NR_2$ (where each R is independently selected from H and $C_{1-5}$ alkyl), hydroxyl, —SH and —CN groups. More preferably, $R_2$ is selected from the group consisting of $CH_3$, Cl, $CH_2CH_3$, $CH_2CH_2CH_3$, $CH(CH_3)_2$, $NH_2$, $NHCH_3$, $N(CH_3)_2$, OH, SH, CN, F, Br and I; and $R_3$ is selected from the group consisting of F, Cl, CN, $CH_3$, $CH_2CH_3$, $CH_2CH_2CH_3$, $CH(CH_3)_2$, $NH_2$, $NHCH_3$, $N(CH_3)_2$, OH, Br, I and SH. More preferably still $R_2$ is selected from the group consisting of $CH_3$, Cl, $NH_2$, OH, SH, CN and F; and $R_3$ is selected from the group consisting of F, Cl, CN, $CH_3$, $NH_2$, OH and SH. Most preferably $R_2$ is selected from the group consisting of $CH_3$ and Cl; and $R_3$ is selected from the group consisting of F, Cl and CN.

A preferred combination of $R_4$, $R_5$, $R_6$ and $R_7$ in formula (ID) is that wherein:

$R_4$ and $R_5$ are independently selected from hydrogen, $C_{1-5}$ alkyl, $C_{2-5}$ alkenyl, $C_{2-5}$ alkynyl and $C_{1-4}$ alkoxyl;

$R_6$ is a $C_{6-10}$ aryl group or a heteroaryl group that contains 5 to 10 ring atoms, said aryl or heteroaryl group being unsubstituted or substituted by one or more (e.g. 1 to 5) substituents selected from halogen atoms and $C_{1-5}$ alkyl, $C_{1-4}$ alkoxy, $C_{1-4}$ alkylthiol, $-NR_2$ (where each R is independently selected from H and $C_{1-5}$ alkyl), hydroxyl, thiol (SH), nitrile (CN), nitro and sulfonic acid groups; and $R_7$ is a phenyl, pyridinyl, pyridazinyl, pyrimidinyl pyrazinyl or triazinyl group that is unsubstituted or substituted by one or more (e.g. 1 to 4) substituents selected from halogen atoms and $C_{1-5}$ alkyl, $C_{1-4}$ alkoxy, $C_{1-4}$ alkylthiol, $-NR_2$ (where each R is independently selected from H and $C_{1-5}$ alkyl), hydroxyl, thiol (SH), nitrile (CN), nitro and sulfonic acid groups.

A more preferred combination of $R_4$, $R_5$, $R_6$ and $R_7$ in formula (ID) is that wherein:

$R_4$ is $C_{2-4}$ alkyl, $C_{2-4}$ alkenyl, $C_{2-4}$ alkynyl or $C_{1-3}$ alkoxy;

$R_5$ is hydrogen, methyl, ethyl, ethenyl, ethynyl or methoxy;

$R_6$ is selected from the following 6-1 to 6-12:

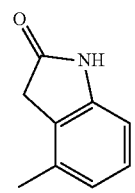

(6-1)

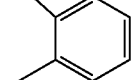

(6-2)

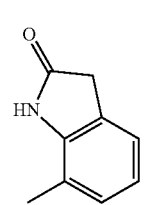

(6-3)

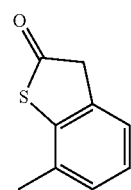

(6-4)

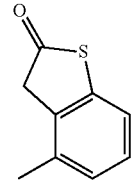

(6-5)

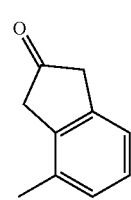

-continued

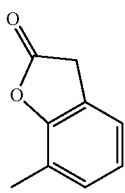
(6-6)

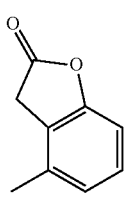
(6-7)

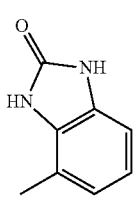
(6-8)

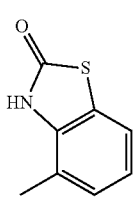
(6-9)

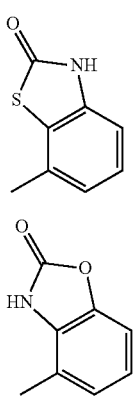
(6-10)

(6-11)

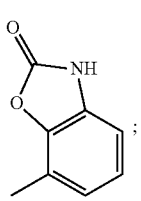
(6-12)

in which one or more (e.g. 1 to 3) H-groups bound to ring atoms are optionally replaced by substituents selected from halogen atoms and $C_{1-5}$ alkyl, $C_{1-4}$ alkoxy, $C_{1-4}$ alkylthiol, $-NR_2$ (where each R is independently selected from H and $C_{1-5}$ alkyl), hydroxyl, thiol (SH), nitrile (CN), nitro and sulfonic acid groups; and $R_7$ is a phenyl, pyridinyl, pyridazinyl, pyrimidinyl pyrazinyl or triazinyl group that is unsubstituted or substituted by one or more (e.g. 1 to 4) substituents selected from halogen atoms and $C_{1-5}$ alkyl, $-NR_2$ (where each R is independently selected from H and $C_{1-5}$ alkyl), hydroxyl, $-SH$ and $-CN$ groups.

A still more preferred combination of $R_4$, $R_5$, $R_6$ and $R_7$ in formula (ID) is that wherein:

$R_4$ is n-propyl, $-CH=CH-CH_3$, $-C\equiv C=CH_2$ or ethoxy;

$R_5$ is hydrogen, methyl or ethyl;

$R_6$ is a 4-(2-oxindolyl) group that is unsubstituted or substituted by one or more (e.g. 1 to 3) substituents selected from halogen atoms and $C_{1-5}$ alkyl, $-NR_2$ (where each R is independently selected from H and $C_{1-5}$ alkyl), and hydroxyl groups; and $R_7$ is a group of formula $R_7''$

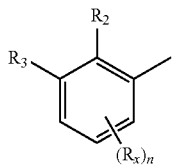
($R_7''$)

wherein $R_2$ and $R_3$ are substituents, each $R_x$ is an independently selected substituent, n is an integer of from 0 to 3, and each substituent is independently selected from halogen atoms and $C_{1-5}$ alkyl, $-NR_2$ (where each R is independently selected from H and $C_{1-5}$ alkyl), hydroxyl, $-SH$ and $-CN$ groups.

In one exemplary aspect, the compound has the formula (I)

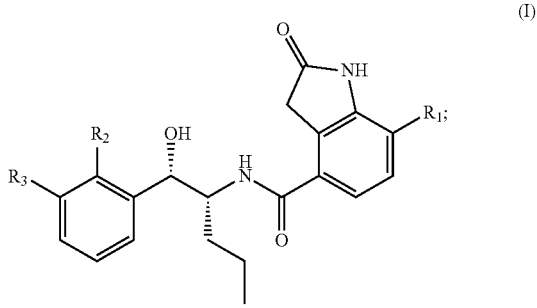
(I)

wherein $R_1$ is selected from the group consisting of H, F, $CH_3$, $CH_2CH_3$, $CH_2CH_2CH_3$, $CH(CH_3)_2$, $NH_2$, $NHCH_3$, $N(CH_3)_2$, OH, Cl, Br and I;

$R_2$ is selected from the group consisting of $CH_3$, Cl, $CH_2CH_3$, $CH_2CH_2CH_3$, $CH(CH_3)_2$, $NH_2$, $NHCH_3$, $N(CH_3)_2$, OH, SH, CN, F, Br and I; and $R_3$ is selected from the group consisting of F, Cl, CN, $CH_3$, $CH_2CH_3$, $CH_2CH_2CH_3$, $CH(CH_3)_2$, $NH_2$, $NHCH_3$, $N(CH_3)_2$, OH, Br, I and SH.

Preferably in formula (I), $R_1$ is selected from the group consisting of H, F, $CH_3$, $NH_2$, OH and Cl. Preferably in formula (I), $R_2$ is selected from the group consisting of $CH_3$, Cl, $NH_2$, OH, SH, CN and F. Preferably in formula (I), $R_3$ is selected from the group consisting of F, Cl, CN, $CH_3$, $NH_2$, OH and SH. Preferably in formula (I), $R_1$ is selected from the group consisting of H, F, $CH_3$, $NH_2$, OH and Cl; and $R_2$ is selected from the group consisting of $CH_3$, Cl, $NH_2$, OH, SH, CN and F; and $R_3$ is selected from the group consisting of F, Cl, CN, $CH_3$, $NH_2$, OH and SH.

Particularly preferably in formula (I), $R_1$ is selected from the group consisting of H and F. Particularly preferably in formula (I), $R_2$ is selected from the group consisting of $CH_3$ and Cl. Particularly preferably in formula (I), $R_3$ is selected from the group consisting of F, Cl and CN. Particularly preferably in formula (I), $R_1$ is selected from the group consisting of H and F; and $R_2$ is selected from the group consisting of $CH_3$ and Cl; and $R_3$ is selected from the group consisting of F, Cl and CN.

Non-limiting, exemplary compounds of formula (I) are those in which: (a) $R_1$ is H, $R_2$ is $CH_3$ and $R_3$ is F; (b) $R_1$ is H, $R_2$ is $CH_3$ and $R_3$ is Cl; (c) $R_1$ is F, $R_2$ is Cl and $R_3$ is CN; and (d) $R_1$ is F, $R_2$ is Cl and $R_3$ is F.

Therapeutic Indications

The compounds of the invention may be useful in treating diseases mediated by alpha 1 antitrypsin, including alpha-1-antitrypsin deficiency. Diseases mediated by alpha-1 antitrypsin include alpha-1 antitrypsin deficiency, liver dysfunction, fibrosis, cirrhosis, liver failure and hepatocellular carcinoma, diseases of lung, dysfunction and inflammation including asthma, COPD, emphysema and lung cancer, inflammatory conditions of the skin including dermatitis and pruritus. Usually, diseases mediated by alpha-1 antitrypsin will be as a result of a mutation in the alpha-1 antitrypsin gene and conforming to the general class of diseases termed 'serpinopathies'.

The compounds of this invention may be particularly useful in the treatment of respiratory disease including COPD and emphysema.

More particularly the compounds of the invention maybe useful in the treatment of disorders due to mutant forms of alpha 1 antitrypsin, including the mutant Z-AT form of alpha 1 antitrypsin, thus being potentially useful in treating diseases associated with Z-AT, particularly diseases of the liver including jaundice, liver failure, liver cirrhosis, autoimmune hepatitis, and hepatocellular carcinoma.

Alpha-1 antitrypsin deficiency affects 1 in 2000 people of Northern European descent, leading to liver and lung disease. Over 100 different mutations have been identified in the SERPINA1 gene that encodes $\alpha_1$-antitrypsin but an estimated 95% of severe deficiency results from the Z-AT form (Glu342Lys). This amino acid substitution disturbs the folding of $\alpha_1$-antitrypsin resulting in the secretion of only ~15% mature protein. Most of the remaining protein is degraded via the ERAD-proteasome pathway, but approximately 15% forms ordered polymers that accumulate within the endoplasmic reticulum of hepatocytes. The consequent deficiency of an important protease inhibitor within the circulation results in insufficient protection of the lungs from neutrophil elastase, leading to emphysema. The accumulation of polymers within hepatocytes is cytotoxic to the cells causing neonatal hepatitis, cirrhosis and hepatocellular carcinoma. The intrahepatic polymers also sensitise the liver to damage from environmental insults such as alcohol, fat or viral hepatitis.

The inhibition of the target protease—elastase—by $\alpha_1$-antitrypsin involves a subversion of the proteolytic mechanism: following nucleophilic attack on a recognition sequence in the $\alpha_1$-antitrypsin reactive centre loop (RCL), the two proteins become covalently attached through an ester bond. Rapid insertion of the RCL into central j-sheet A ensues, converting it from a 5-stranded to 6-stranded configuration. The concomitant translocation of the protease from one pole of the serpin to the other, and compression of its active site, prevents hydrolysis of this normally transient linkage; the two are thereby irreversibly trapped an inactivated protease-serpin covalent complex. The Z mutation lies at the head of strand 5 of f-sheet A. It perturbs the local environment, allowing $\alpha_1$-antitrypsin to populate an unstable intermediate (that has been termed the M* state), in which f-sheet A opens and the upper part of helix F unwinds. It remains to be established whether incorporation of the RCL is intermolecular—resulting in a loop-sheet dimer which extends to form longer polymers—or intramolecular with a domain-swap of the C-terminal region providing the inter-subunit linkage for the pathological polymer that deposits in liver tissue. Other forms of polymerization by different mutants of $\alpha_1$-antitrypsin may be possible. The ability of a destabilised β-sheet A to incorporate the reactive centre loop is an obligate step in the formation of polymers. This renders the mechanism of polymerisation closely related to that of protease inhibition: in both, the reactive centre loop is a central actor in a thermodynamically-driven transition between a moderately stable and a hyper-stable conformation.

The commonality between the physiological mechanism of serpin inhibition and the pathological generation of polymer is also observed within other members of the serpin superfamily and gives rise to class of related pathologies termed serpinopathies. These include familial encephalopathy with neuroserpin inclusion bodies (FENIB) caused by polymerogenic mutations in neuroserpin and forms of thrombosis caused by polymerisation and deficiency of antithrombin.

Therapy and Methods of Treatment

This invention also provides a compound of the invention, for use in therapy. This invention specifically provides for the use of a compound of the invention, as an active therapeutic substance in the treatment of diseases mediated by alpha-1-antitrypsin.

The invention also provides for the use of a compound of the invention in the manufacture of a medicament for use in the treatment of diseases mediated by alpha-1-antitrypsin.

In a further aspect there is provided a combination comprising a compound of the invention and at least one further therapeutic agent useful in the treatment of diseases mediated by alpha-1-antitrypsin.

In a further aspect there is provided a combination comprising a compound of the invention and at least one further therapeutic agent useful in the treatment of diseases mediated by alpha-1-antitrypsin, for use in the treatment of diseases mediated by alpha-1-antitrypsin.

In a further aspect there is provided the use of a combination comprising a compound of the invention and at least one further therapeutic agent useful in the treatment of COPD in the manufacture of a medicament for the treatment of diseases mediated by alpha-1-antitrypsin.

In a further aspect there is provided a method of treating COPD comprising administering to a human in need thereof a therapeutically effective amount of a combination comprising a compound of the invention and at least one further therapeutic agent useful in the treatment of diseases mediated by alpha-1-antitrypsin.

In a further aspect there is provided a pharmaceutical composition comprising a combination comprising a compound of the invention and at least one further therapeutic agent useful in the treatment of diseases mediated alpha-1-antitrypsin and one or more of pharmaceutically acceptable excipients.

Respiratory Disease

For the treatment of respiratory disease, including COPD, compounds or pharmaceutical compositions of the invention may be administered together with one or more bronchodilators, or pharmaceutical compositions thereof. For example, compounds of the invention may be formulated together with one or more bronchodilators in a single composition, such as a dry powder for inhalation. Alternatively, a pharmaceutical composition comprising a compound of the invention may be administered in conjunction with a pharmaceutical composition comprising one or more bronchodilators, either simultaneously or sequentially. In a further alternative, a composition comprising a compound of the invention and a bronchodilator may be administered in conjunction with a pharmaceutical composition comprising a further bronchodilator. In one embodiment, a pharmaceutical composition comprising a compound of the invention and a pharmaceutical composition comprising one or more bronchodilators may each be held in device suitable for the simultaneous administration of both compositions via inhalation. In a further embodiment, a pharmaceutical composition comprising a compound of the invention together with a bronchodilator and a pharmaceutical composition comprising a further bronchodilator may each be held in device suitable for the simultaneous administration of both compositions via inhalation.

Suitable bronchodilators for administration together with compounds of the invention include $\beta_2$-adrenoreceptor agonists and anticholinergic agents. Examples of $\beta_2$-adrenoreceptor agonists, include, for example, vilanterol, salmeterol, salbutamol, formoterol, salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. Examples of anticholinergic agents include umeclidinium (for example as the bromide), ipratropium (for example, as the bromide), oxitropium (for example, as the bromide) and tiotropium (for example, as the bromide). In one embodiment, a compound of the invention may be administered together with a $\beta_2$-adrenoreceptor agonist, such as vilanterol, and an anticholinergic agent, such as, umeclidinium.

Liver Disease

For the treatment of liver disease the compounds or pharmaceutical compositions of the invention may be administered with other therapeutic agents useful in treating these diseases.

General Synthetic Methods

Compounds of general formula (I) may be prepared by methods known in the art of organic synthesis. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3$^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Other compounds of the invention can also be prepared using methods routinely known in the art and, where applicable, with reference to the principles and specific reactions described herein.

Method for Identifying a Drug Candidate Compound

The present inventors' discovery that compounds of the invention inhibit $\alpha_1$-antitrypsin polymerisation by binding to the $\alpha_1$-antitrypsin protein at a particular binding site also gives rise to an assay method based on determining the capability of an arbitrary drug candidate compound to bind to the same site on the protein.

Thus, the present invention further provides a method for identifying a drug candidate compound. In the method, the drug candidate compound is contacted with $\alpha_1$-antitrypsin to form a complex between the drug candidate compound and $\alpha_1$-antitrypsin. The $\alpha_1$-antitrypsin is a protein comprising SEQ ID NO: 1 as defined elsewhere herein (or a derivative of this sequence with one or more amino acid substitutions). Preferably the step of contacting the drug candidate compound with $\alpha_1$-antitrypsin comprises forming a crystal of $\alpha_1$-antitrypsin and contacting said crystal with said drug candidate.

Subsequently the method comprises resolving the structure of the complex, which can be done routinely using crystal structure resolution methods well known in the art (see also, for instance, Example 2 of this application).

Finally, the method comprises determining whether, in the complex, the drug candidate compound is present in the binding site as defined herein. If the drug candidate compound is present in the binding site, then this is indicative of a compound that may be capable of inhibiting $\alpha_1$-antitrypsin polymerisation, and thus having beneficial therapeutic properties, by analogy with the compounds of the present invention as discussed elsewhere herein.

EXAMPLES

Example 1

General Methods

Unless stated otherwise, starting materials were commercially available. All solvents and commercial reagents were of laboratory grade and were used as received. Compounds of formula (I) may be synthesised substantially according to Reaction Scheme 1 from an amide coupling of the corresponding amino alcohol and corresponding benzoic acid.

Reaction scheme 1

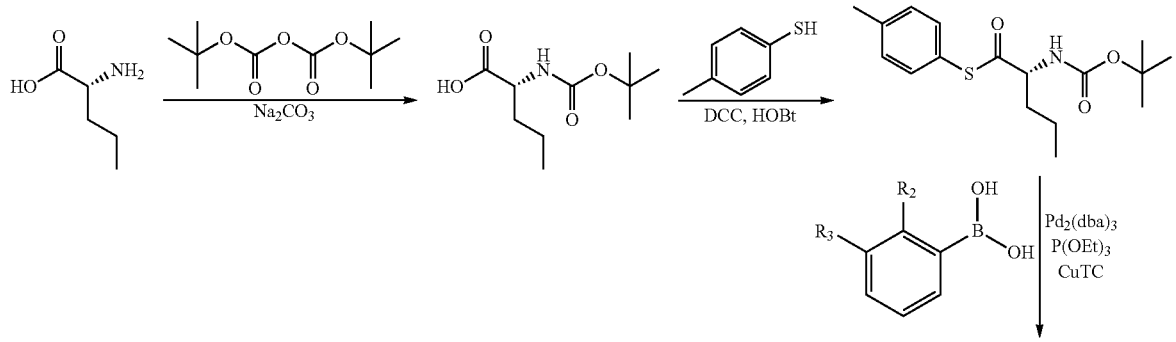

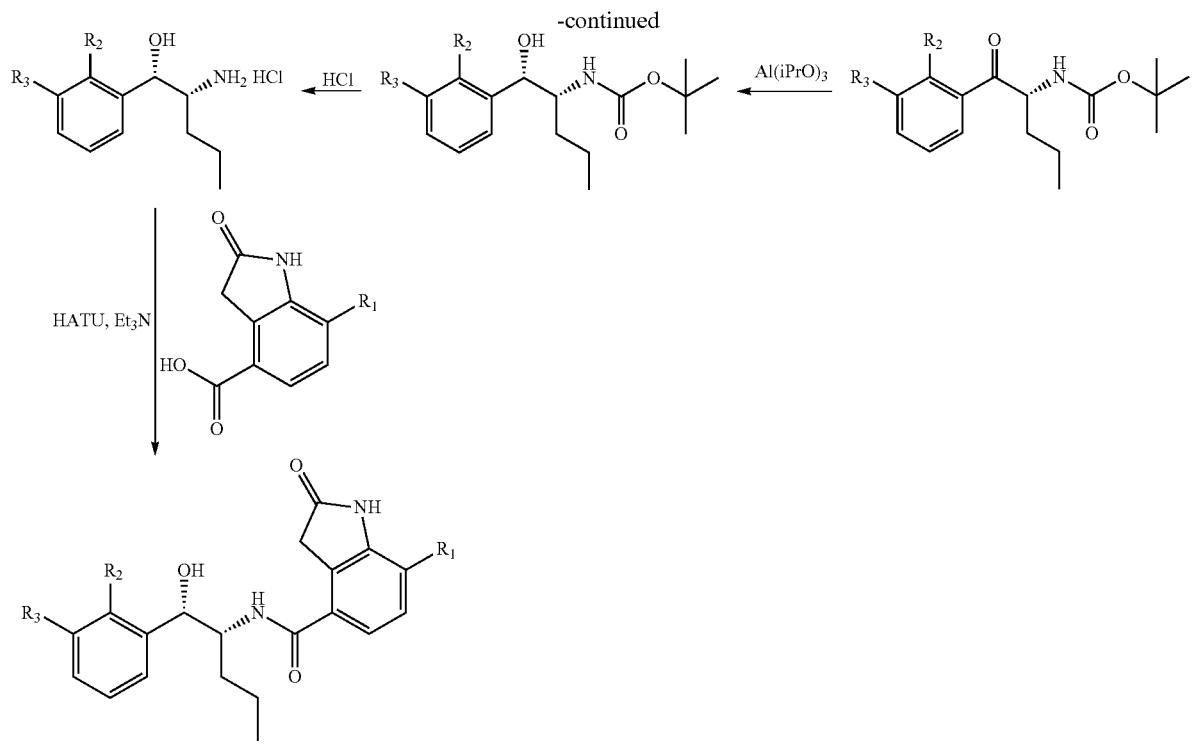

Abbreviations

DMSO Dimethyl sulfoxide
HATU N-[(Dimethylamino)-1H-1,2,3-triazolo-[4,5-b]pyridin-1-ylmethylene]-N-methylmethanaminium hexafluorophosphate N-oxide
r.t. Room temperature
Rt Retention time LCMS Methods

| Method | Description |
|---|---|
| A | Column: Acquity UPLC CSH C18 column (50 mm × 2.1 mm i.d. 1.7 μm particle size) Mobile Phase: A: 0.1% Formic acid in water; B: 0.1% Formic acid in Acetonitrile Time (min)/%B: 0/3%, 1.5/99.9%, 1.9/99.9%, 2.0/3.0% Column Temp: 40° C. Flow Rate: 1.0 mL/min |
| B | Column: Acquity UPLC BEH C18 column (50 mm × 2.1 mm i.d. 1.7 μm particle size) Mobile Phase: A: 0.1% v/v ammonia aqueous solution pH 10; B: Acetonitrile Time (min)/%B: 0/3%, 1.5/99.9%, 1.9/99.9%, 2.0/3.0% Column Temp: 40° C. Flow Rate: 1.0 mL/min |
| C | Column: Acquity UPLC BEH C18 (50 mm × 2.1 mm, 1.7 μm particle size) Mobile Phase: A: 0.1% Formic acid in water; B: 0.1% Formic acid in Acetonitrile Time (min)/%B: 0/3.0%, 1.5/100.0%, 1.9/100.0%, 2.0/3% Column Temp: 40° C. Flow Rate: 1.0 mL/min |

Chiral HPLC Method

| Method | Description |
|---|---|
| Chiral HPLC | Column Chiralpak AS-H (25 × 0.46 cm, 5 um particle size) Mobile phase: n-Hexane/(Ethanol + 0.1% isopropylamine) 65/35% v/v Flow rate: 1.0 ml/min |

Compound 1

N-[(1S,2R)-1-(3 fluoro-2-methylphenyl)-1-hydroxypentan-2-yl]-2-oxo-2,3-dihydro-1H-indole-4-carboxamide

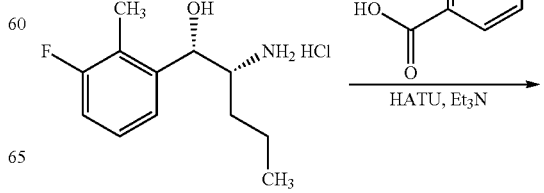

-continued

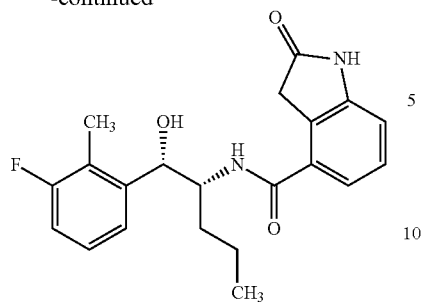

In a round bottom flask, to a solution of (1S,2R)-2-amino-1-(3-fluoro-2-methylphenyl)pentan-1-ol hydrochloride (intermediate 1, 12.9 g, 51.9 mmol), 2-Oxoindoline-4-carboxylic acid (9.2 g, 51.9 mmol) and triethylamine (10.5 g, 103.9 mmol) in dimethylformamide (100 ml) at 0° C., HATU (19.8 g, 51.9 mmol) was added. The reaction mixture was stirred at 0° C. for 1 h and then was diluted with ethyl acetate (200 ml). The solution was washed with a saturated solution of NaHCO$_3$ (100 ml) and brine (2×100 ml). The organic portion was dried over sodium sulfate, filtered and evaporated under reduced pressure to obtain crude material which was purified by flash Chromatography (Biotage Isolera, 340 g cartridge, Dichloromethane/Acetonitrile 80/20 to 40/60 as eluent) to afford N-[(1S,2R)-1-(3-fluoro-2-methylphenyl)-1-hydroxypentan-2-yl]-2-oxo-2,3-dihydro-1H-indole-4-carboxamide as white solid (12.5 g, Y=65.0%).

In a round bottom flask, (12.5 g, 33.74 mmol) was suspended in ethyl acetate (100 ml) at rt. The suspension was heated to 60° C. and ethyl acetate was added until the mixture became homogeneous (≈200 ml of solvent totally). The solution was left to cool at r.t. overnight and the white precipitate formed was collected by suction filtration. The solid was stored in oven at 40° C. under vacuum to obtain crystalline N-[(1S,2R)-1-(3-fluoro-2-methylphenyl)-1-hydroxypentan-2-yl]-2-oxo-2,3-dihydro-1H-indole-4-carboxamide as white solid (10.8 g, >98% ee, 87% recovery).

LCMS: Rt 0.90 min, MH+ 371 (Method A)

$^1$H NMR (500 MHz, DMSO-d$_6$) δ ppm 0.80 (t, J=7.34 Hz, 3H), 1.07-1.21 (m, 1H), 1.30-1.43 (m, 1H), 1.45-1.54 (m, 1H), 1.56-1.67 (m, 1H), 2.31 (d, J=1.51 Hz, 3H), 3.46 (s, 2H), 4.06-4.17 (m, 1H), 4.85 (t, J=5.21 Hz, 1H), 5.44 (d, J=4.80 Hz, 1H), 6.89 (d, J=7.68 Hz, 1H), 6.99 (t, J=8.92 Hz, 1H), 7.11-7.25 (m, 3H), 7.28 (d, J=7.68 Hz, 1H), 7.97 (d, J=8.92 Hz, 1H), 10.45 (s, 1H).

Chiral HPLC: Rt 6.3 min

Intermediate 1

(1S,2R)-2-amino-1-(3-fluoro-2-methylphenyl)pentan-1-ol hydrochloride

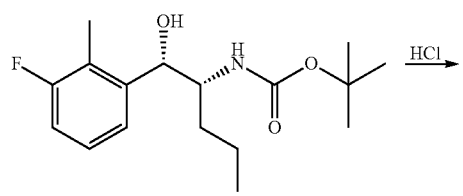

-continued

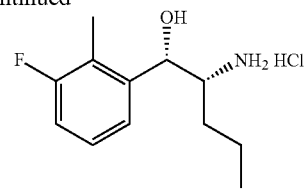

In a round bottom flask, tert-butyl ((1S,2R)-1-(3-fluoro-2-methylphenyl)-1-hydroxypentan-2-yl)carbamate (intermediate 2, 15.8 g, 50.74 mmol) was dissolved in HCl in dioxane 4 M (100 ml) at 0° C. The mixture was stirred for 2 h at the same temperature and the solvent was evaporated. The residue was suspended in 300 ml of diethyl ether and stirred for 1 h. The suspension was filtered to obtain (1S,2R)-2-amino-1-(3-fluoro-2-methylphenyl)pentan-1-ol hydrochloride as a white solid (11.9 g, Y=95.0%).

LCMS: Rt 0.85 min, MH+ 212 (Method B)

Intermediate 2 tert-butyl ((1S,2R)-1-(3-fluoro-2-methylphenyl)-1-hydroxypentan-2-yl)carbamate

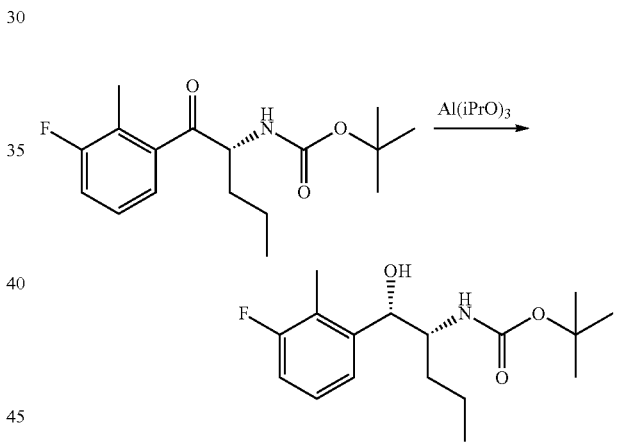

(R)-tert-butyl (1-(3-fluoro-2-methylphenyl)-1-oxopentan-2-yl)carbamate (intermediate 3, 18.7 g, 60.4 mmol) was dissolved in toluene (150 ml) in a round bottom flask, and isopropanol (100 ml) at r.t. and aluminum isopropoxide (49.4 g, 241.8 mmol) were added. The solution was stirred at 50° C. for 16 h and then it was poured into a NH$_4$Cl sat. solution and extracted with ethyl acetate (4×300 ml). The organic portions were collected, dried over sodium sulfate and the solvent was removed under reduced pressure to obtain crude material named as pale yellow oil. This crude material was purified by flash Chromatography (Biotage Isolera, 340 g cartridge, Cyclohexane/Ethyl Acetate 80/20 to 50/50 as eluent) to afford tert-butyl ((1S,2R)-1-(3-fluoro-2-methylphenyl)-1-hydroxypentan-2-yl)carbamate as a colourless oil (15.8 g, Y=84.0%)

LCMS: Rt 1.16 min, MH+ 312 (Method A)

Intermediate 3

(R)-tert-butyl (1-(3-fluoro-2-methylphenyl)-1-oxopentan-2-yl)carbamate

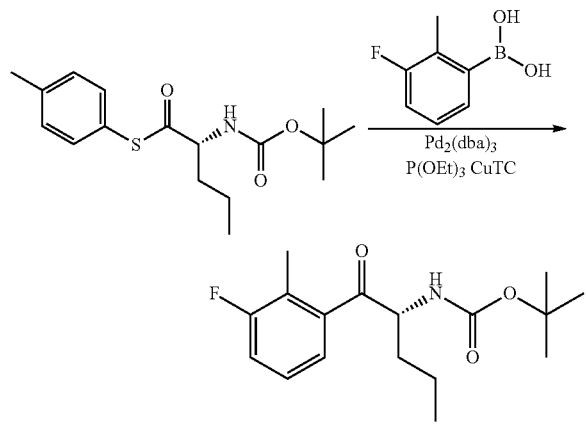

To a mixture of (3-fluoro-2-methylphenyl)boronic acid (intermediate 4, 50 g, 0.32 mol) in a round bottom flask, (R)—S-p-tolyl 2-((tert-butoxycarbonyl)amino)pentanethioate (53.2 g, 0.16 mol), tris(dibenzylideneacetone)dipalladium(0) (7.3 g, 8.0 mmol), and copper(I) thiophene-2-carboxylate (61.0 g, 0.32 mol) in 1,4-Dioxane (500 ml) at r.t., triethyl phosphite (10.6 g, 64.0 mmol) was added. The reaction mixture was stirred at rt for 4 h and then was filtered over a celite pad. The solvent was evaporated under reduced pressure and the crude was dissolved in ethyl acetate (500 ml); the solution was washed with water (500 ml) and brine (2×500 ml). The organic portion was dried over sodium sulfate, filtered and evaporated under reduced pressure to obtain crude material (100 g) as black oil. A 65 g batch of the crude material was purified by flash Chromatography (Biotage Isolera, 3×340 g cartridge, Cyclohexane/Dichloromethane 60/40 to 0/100 as eluent) to afford (R)-tert-butyl (1-(3-fluoro-2-methylphenyl)-1-oxopentan-2-yl)carbamate as colourless oil (18.7 g, 60.4 mmol).

LCMS: Rt 1.26 min, MH+ 310 (Method A)

Intermediate 4

(R)—S-p-tolyl 2-((tert-butoxycarbonyl)amino)pentanethioate

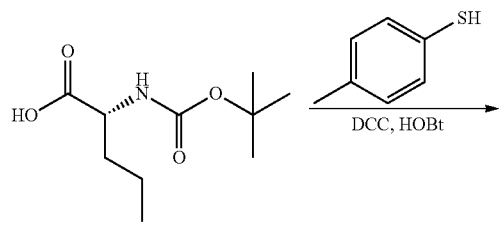

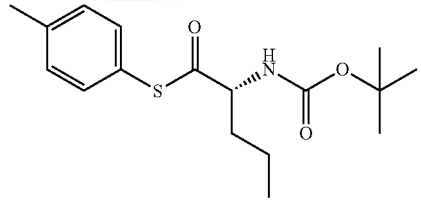

To a solution of (R)-2-((tert-butoxycarbonyl)amino)pentanoic acid (intermediate 5, 85.0 g, 0.39 mol) in ethyl acetate (800 ml) in a round bottom flask, 4-methylbenzene-1-thiol (53.5 g, 0.43 mol) and 1-Hydroxybenzotriazole (50.0 g, 0.59 mol) were added. The mixture was cooled to 0° C. and N,N'-Dicyclohexylcarbodiimide (80.5 g, 0.39 mol) was added. The reaction mixture was stirred at r.t. for 16 h; the white solid formed was then removed by suction filtration. The filtrate was washed with a saturated solution of NaHCO₃ (700 ml), water (700 ml) and brine (700 ml). The organic portion was dried over sodium sulfate, filtered and the solvent was evaporated under reduced pressure to obtain crude material as a white solid. The crude material was purified by flash chromatography (Biotage Isolera, 340 g cartridge, Cyclohexane/Dichloromethane 60/40 to 0/100 as eluent) to afford (R)—S-p-tolyl 2-((tert-butoxycarbonyl)amino)pentanethioate as a white solid (111.0 g, Y=88.0%).

LCMS: Rt 1.30 min, MH+ 324 (Method A)

Intermediate 5

(R)-2-((tert-butoxycarbonyl)amino)pentanoic acid

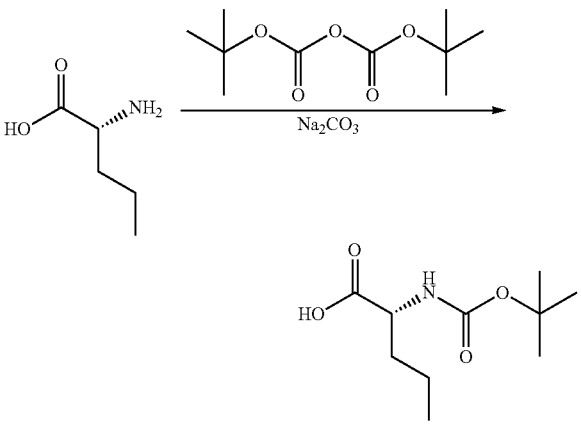

In a round bottom flask, to a suspension of (2R)-2-aminopentanoic acid (75.0 g, 0.64 mol) was put into a round bottom flask in water (250 ml) at r.t., sodium carbonate (68.0 g, 0.64 mol) was added. A solution of di-tert-butyl dicarbonate (139.9 g, 0.64 mol) in tetrahydrofuran (400 ml) was added dropwise over one hour. The reaction mixture was stirred at r.t. for 24 h and then concentrated under reduced pressure (approx. 400 ml). A saturated solution of citric acid (300 ml) was added until pH reached the value of ≈3. The aqueous layer was washed with ethyl acetate (4×500 ml). The organic portions were collected, dried over magnesium sulfate and evaporated under reduced pressure to obtain (R)-2-((tert-butoxycarbonyl)amino)pentanoic acid as a pale yellow oil (137.0 g, Y=98.6%).

LCMS: Rt 0.82 min, MH+ 218 (Method A)

Similarly Prepared Were:

sulphate precipitation, thiol exchange fractionation, and anion exchange fractionation.

Purified Z-A1AT was diluted to 5 nM in PBS buffer with 0.01% Tween-20 and mixed with different concentrations of

| Example n° | structure | name | Retention time (min) | Molecular ion + Identity | LCMS Method |
|---|---|---|---|---|---|
| Compound 2 | *(structure)* | N-((1S,2R)-1-(3-chloro-2-methylphenyl)-1-hydroxypentan-2-yl)-2-oxoindoline-4-carboxamide | 0.93 | 387 (MH+) | C |
| Compound 3 | *(structure)* | N-((1S,2R)-1-(2-chloro-3-cyanophenyl)-1-hydroxypentan-2-yl)-7-fluoro-2-oxoindoline-4-carboxamide | 0.82 | 416 (MH+) | C |
| Compound 4 | *(structure)* | N-((1S,2R)-1-(2-chloro-3-fluorophenyl)-1-hydroxypentan-2-yl)-7-fluoro-2-oxoindoline-4-carboxamide | 0.89 | 409 (MH+) | C |

The potencies of the compounds of the invention for inhibition of Z-alpha-1-antitrypsin (Z-A1AT) polymerisation can be determined by a time-resolved fluorescence energy transfer (TR-FRET) assay performed on purified Z-A1AT as described herein. All compounds of formula (I) have demonstrated inhibitory activity of Z-A1AT polymerisation in-vitro with a half maximal inhibitory concentration ($IC_{50}$) of less than one micromolar (1 μM). Mean activity data for the assay described below for compounds 1-4:

| Compound 1 | PIC50 | 8.3 | SD = .18, Range 8.0-8.4 |
|---|---|---|---|
| Compound 2 | PIC50 | 8.6 | SD = .15, Range 8.4-9.9 |
| Compound 3 | PIC50 | 8.5 | SD = .1 Range 8.4-8.6 |
| Compound 4 | PIC50 | 8.2 | SD = .21, Range 7.8-8.5 |

Inhibition of Z-Alpha-1-Antitrypsin Polymerisation Assay Protocol

Z-alpha-1-antitrypsin was purified from human plasma of donors homozygous for the Z-A1AT form. The purification was performed according to a published protocol (Lomas et al. *Biochemistry* 1993; 32:500-508) involving ammonium inhibitor compounds dissolved in DMSO, in 384-well assay plates. Following incubation for 72 hours at 37° C., the amount of Z-A1AT polymer was detected using a time-resolved fluorescence resonance energy transfer (TR-FRET) assay format, by adding an antibody detection mix to the assay plates. The detection mix contained an A1AT-polymer specific monoclonal antibody (Miranda et al. *Hepatology* 2010; 52: 1078-1088), Terbium-labelled anti-mouse antibody, a polyclonal rabbit anti-A1AT antibody, and an Alexa488-labelled anti-rabbit antibody. TR-FRET data were normalised to controls (DMSO vehicle control giving 0% inhibition, saturating concentrations of an active compound giving 100% inhibition), and IC50 values were derived by fitting 4-parameter logistic curves to the normalised data.

Example 2

Introduction

The aim of this work was to develop a small molecule corrector of Z $α_1$-antitrypsin folding able to block the formation of polymer within the endoplasmic reticulum of hepatocytes and that was suitable for oral dosing as a potential treatment for $\alpha_1$-antitrypsin deficiency. To achieve this a number of challenges needed to be overcome: (i) the specific form of the protein representing the drug target is a highly mobile folding intermediate, located in the endoplasmic reticulum; (ii) the targeted pharmacology involves prevention of a large protein-protein interaction and the requirement that a molecule have drug-like properties to enable oral dosing greatly restricts suitable chemical space; (iii) as a non-classical drug target, small molecule binders may well not be well-represented in compound screening libraries; (iv) the relatively high concentration of circulating monomeric Z $\alpha_1$-antitrypsin (~5 µM), even in individuals with severe plasma deficiency, represents a high affinity sink for compound, restricting its access to the target in the hepatocyte and requiring high total blood concentrations of drug to achieve sufficient free drug concentration and target engagement in the liver.

Reported herein are the first small molecule drug-like correctors of Z $\alpha_1$-antitrypsin folding obtained via optimisation of hits from an Encoded Library Technology screen, that are suitable for oral delivery, correct folding in human patient iPSC-derived hepatocytes and increase circulating Z $\alpha_1$-antitrypsin levels in a transgenic mouse model of $\alpha_1$-antitrypsin deficiency.

Materials and Methods

Alpha$_1$-antitrypsin was purified from the plasma of ZZ and MM $\alpha_1$-antitrypsin homozygotes as described in Lomas et al., Biochemistry. 1993; 32:500-8. Recombinant Cys232Ser $\alpha_1$-antitrypsin was expressed and purified as detailed in Irving et al. Methods Enzymol. 2011; 501:421-66 and Haq et al. Biosci Rep. 2013; 33(3):e00046.

"Compound 1" is N-[(1S,2R)-1-(3-fluoro-2-methylphenyl)-1-hydroxypentan-2-yl]-2-oxo-2,3-dihydro-1H-indole-4-carboxamide

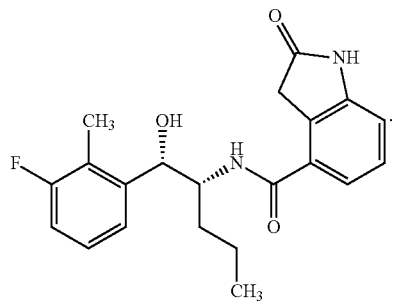 [SMILES: CCC[C@@H](NC(=O)c1cccc2c1CC(=O)N2)[C@@H](O)c1cccc(F)c1C]

DNA-Encoded Library Technology (ELT) Screen

An encoded library technology (ELT) screen of approximately 10 million compounds was used to identify small molecules that will stabilise monomeric Z $\alpha_1$-antitrypsin at 37 and 41° C. The strongest binders were eluted, identified by their DNA tag and synthesised.

Antibody-Based Assessment of Polymerisation of Z $\alpha_1$-Antitrypsin

An antibody-based time-resolved fluorescence resonance energy transfer (TR-FRET) assay was used to monitor the polymerisation of 5 nM Z $\alpha_1$-antitrypsin following incubation with varying concentrations of compounds at 37° C. for 72 hours. This assay used the 2C1 monoclonal antibody that is specific to pathological polymers of $\alpha_1$-antitrypsin (Miranda et al. *Hepatology* 2010; 52: 1078-1088), a polyclonal antibody that binds to all forms of $\alpha_1$-antitrypsin, an anti-mouse IgG fluorescence donor (Eu-W1024) and an anti-rabbit IgG acceptor (APC).

Biochemical Competition Binding Assay for Z $\alpha_1$-Antitrypsin and M $\alpha_1$-Antitrypsin A fluorescent derivative of compound 1 was prepared by derivatizing compound 1 at its ring nitrogen atom with an Alexa Fluor 488 label via a short organic linker group.

A serial dilution of test compounds in DMSO was diluted 25-fold with assay buffer, and 2.5 µl of this intermediate dilution transferred to a black, low-volume 384-well microtitre plate (Greiner BioOne; product no. 784076). 5 µl of a pre-mixed solution of assay buffer containing 2.3 nM of the monoclonal antibody 3C11 binding to antitrypsin, 3 nM of LanthaScreen Terbium-labeled Anti-mouse IgG which will bind to the 3C11 antibody (Invitrogen), as well as either 2 nM Z-a1AT or 10 nM M-a1AT were added using a Thermo Multidrop dispenser (ThermoFisher). Plates were incubated at room temperature for 30 min, then 2.5 µl of ligand solution were added, containing either 40 nM (for Z $\alpha_1$-antitrypsin) or 2 µM (for M $\alpha_1$-antitrypsin) of the fluorescent derivative of compound 1, using a Thermo Multidrop dispenser.

Plates were sealed and incubated overnight at room temperature, or for 3 days at 4° C. then 6 hours at room temperature. In the absence of competing compound, energy transfer can occur between the Terbium- and Alexa488 fluorophores. Compounds competing with the fluorescent derivative of compound 1 inhibit this signal. The TR-FRET signal was read on an Envision plate reader, by excitation of Terbium at 337 nm and detection of emission at 520 nm and 495 nm.

Dissociation constants ($K_D$) for the affinity of compounds to Z-a1AT or M-a1AT protein were derived from the pIC50 values according to the Cheng-Prusoff equation, taking into account the concentration of fluorescent ligand used in relation to its affinity as determined in independent Fluorescence Polarisation and TR-FRET experiments:

$$K_D(\text{compound}) = 10^{-pIC50(compound)}/(1-([\text{Ligand}]/K_D(\text{Ligand})))$$

Compound Association Experiments

The intrinsic tryptophan fluorescence of $\alpha_1$-antitrypsin is dominated by Trp194 in the breach region (Tew et al. J Mol Biol. 2001 Nov. 9; 313(5):1161-9) and can be used to monitor the progress of compound binding. Plasma M and Z $\alpha_1$-antitrypsin were diluted to 0.2 mg/ml in 100 µM PBS, and Compound 1 (or an equivalent volume of DMSO) added to a concentration of 10 µM. Fluorescence ($\lambda_{ex}$=280 nm, $\lambda_{em}$=330 nm) was monitored for at least 2 hours, and the half-time of change was calculated.

Kinetic data in stopped flow experiments were fitted to exponential decay curves with offset and linear slope, to account for a constant drift in the background, resulting in observed pseudo-first-order rate constants k(obs):

$$y = A_0 \cdot e^{-k(obs)t} + \text{slope} \cdot t + \text{offset}$$

where t=time and Ao=amplitude at t=0. The second-order on-rate was then obtained as the slope when plotting k(obs) values versus compound concentration. Off-rates were calculated from the on-rates and the $K_D$ values determined from the binding assays.

Cell Biology

CHO Tet-On cells that conditionally express Z $\alpha_1$-antitrypsin (Ordóñez A et al. Hepatology 2013; 57(5):2049-60.) were simultaneously treated with 0.5 µg/mL oxycycline and various concentrations of compounds for 48 hours in 6 well plates. Cells without doxycycline or treated with 1% v/v DMSO acted as controls. The cells were lysed and intracellular Z $\alpha_1$-antitrypsin polymer was evaluated by ELISA sandwich with the 2C1 monoclonal antibody (Miranda et al. Hepatology. 2010; 52:1078-88). Newly synthesised $\alpha_1$-antitrypsin was evaluated by growing cells induced to express Z $\alpha_1$-antitrypsin in DMEM without methionine (Met) and cysteine (Cys) for 1 h and then labelling with 1.3 MBq of $^{35}$S-Met/Cys for 15 min. The cells were then rinsed and incubated in chase medium containing an excess of unlabeled Met and Cys for 0, 2 and 6 h. After the chase period, the medium was collected and cells were harvested. $\alpha_1$-Antitrypsin from the medium and cell lysates was immunoprecipitated with a polyclonal $\alpha_1$-antitrypsin antibody or the 2C1 monoclonal antibody that detects polymers by splitting each sample in two equal parts. Radiolabelled proteins were re-suspended in SDS loading buffer, boiled for 5 min, separated by 10% w/v acrylamide SDS-PAGE, and quantified by autoradiography.

Immunofluorescence Microscopy

CHO-K1 cells were incubated with/without doxycycline to express $\alpha_1$-antitrypsin and with or without the small molecule of interest, fixed with 3.7% v/v formaldehyde in PBS for 15 min, permeabilised with 0.1% v/v Triton X-100 in PBS and then blocked with 10% v/v FBS in PBS for 30 min. Cells were labelled with a rabbit polyclonal antibody to total $\alpha_1$-antitrypsin or the 2C1 monoclonal antibody that detects polymers followed by Texan red conjugated anti-rabbit or FITC labelled anti-mouse secondary antibodies respectively. Cells were imaged using an Axiovert 200 widefield fluorescence microscope (Carl Zeiss Microimaging Inc., Thornwood, NY).

Thermal Stability Experiments

The native state stability of serpins on addition of compounds was investigated by thermal denaturation in the presence of a 5× concentration of SYPRO Orange dye solution (Life Technologies). A final protein concentration of 0.1 mg/ml and 50 uM compound suspended in PBS was used (Nettleship et al. Methods Mol Biol. 2008; 426:299-318). The samples were heated from 25° C.-95° C. at a rate of 1° C./min in three separate experiments on an Eppendorph Mastercycler Realplex4 quantitative real-time PCR instrument, and the fluorescence in the 605±15 nm bin recorded. The midpoint of denaturation (Tm) is the temperature at which the first derivative of fluorescence intensity against temperature reaches a maximum.

Resistance to heat-induced polymerisation was also determined using an end-point constant-temperature assay. Plasma purified M and Z $\alpha_1$-antitrypsin were diluted to 0.2 mg/ml in PBS with 5% v/v glycerol, incubated with 10 μM Compound 1 (or with DMSO alone) for 2 hours and then heated in 20 μl aliquots for a further 4 hours in a thermal cycler with a 48-65° C. gradient applied across the plate. Samples were analysed on a 3-12% w/v acrylamide Bis-Tris Native-PAGE gel (Life Technologies).

Equilibrium Unfolding

Bis-ANS is a dye that reports the appearance of the unfolding intermediate of $\alpha_1$-antitrypsin (Dafforn et al. J Biol Chem. 1999; 274:9548-55.). In a microplate, 10 μl aliquots of M and Z $\alpha_1$-antitrypsin at 0.5 mg/ml with 100 μM bis-ANS and 100 μM Compound 1 (or an equivalent volume of DMSO) were rapidly mixed with various concentrations of guanidine hydrochloride giving a final concentration of 0-6 M denaturant in PBS. Fluorescence intensity measurements of bis-ANS ($\lambda_{ex}$=385 nm, $\lambda_{em}$=490 nm) were recorded once a stable signal was achieved, and the values scaled to lie between 0 and 1.0.

Rapid Refolding

Refolding of $\alpha_1$-antitrypsin in vitro is not fully reversible, due to loss of material from amorphous aggregation, polymerisation and misfolding. These contributions cannot be readily deconvoluted by bulk spectroscopic methods and therefore refolding was evaluated by non-denaturing PAGE. M and Z $\alpha_1$-antitrypsin at 9.6 mg/ml were denatured in 6 M urea and 15 mM sodium phosphate pH 8.0 for 4 hours at room temperature, and 1.25 μl was snap refolded into 250 μl PBS containing 0-50 μM Compound 1 and a normalised concentration of 5% v/v DMSO. After incubation for 1 hour at room temperature samples were analysed by Coomassie-stained 3-12% w/v acrylamide Bis-Tris Native PAGE gel (Life Technologies).

Crystallography

Crystals of recombinant Cys232Ser $\alpha_1$-antitrypsin were grown using the hanging drop vapour diffusion method by combining 1 μl of 12.1 mg/ml protein with 1 μl of reservoir buffer and equilibrating against reservoir buffer, which comprised 0.1 M MES pH 6.0 buffer with 20-22.25% w/v PEG 1500. A crystal that formed in 0.1M MES pH 6.0 with 22.25% w/v PEG 1500 was transferred into a buffer containing 0.09M MES pH6.0, 18% PEG1500, 13.5% glycerol, 5% d6 DMSO and 25 mM of the compound for incubation at 20° C. for 24 hours. The crystals were snap-frozen in liquid nitrogen and data was collected at the Diamond synchrotron 103 beamline.

Specifically, the $\alpha_1$-antitrypsin protein used for the crystallisation experiments corresponded to the M1V variant of M-AT with the following modifications: (a) Cys232 is mutated to Ser (for ease of handling, obviating the need for reducing agents during different assays; the substitution is a conservative one); (b) the signal peptide component (MPSSVSWGILLLAGLCCLVPVSLA) and Glu1 at the N-terminus of mammalian M-AT are not present at the N-terminus of the protein used; (c) the N-terminus of the protein used has a hexahistidine affinity tag for ease of purification and a few amino acids provided by the expression vector, the sequence thereof being MRGSHHHHHHT.

The full sequence of the protein used was thus:

MRGSHHHHHHTDPQGDAAQKTDTSHHDQDHPTFNKITPNLAEFAFSLYRQL

AHQSNSTNIFFSPVSIATAFAMLSLGTKADTHDEILEGLNFNLTEIPEAQI

HEGFQELLRTLNQPDSQLQLTTGNGLFLSEGLKLVDKFLEDVKKLYHSEAF

TVNFGDTEEAKKQINDYVEKGTQGKIVDLVKELDRDTVFALVNYIFFKGKW

ERPFEVKDTEEEDFHVDQVTTVKVPMMKRLGMFNIQHSKKLSSWVLLMKYL

GNATAIFFLPDEGKLQHLENELTHDIITKFLENEDRRSASLHLPKLSITGT

YDLKSVLGQLGITKVFSNGADLSGVTEEAPLKLSKAVHKAVLTIDEKGTEA

AGAMFLEAIPMSIPPEVKFNKPFVFLMIEQNTKSPLFMGKVVNPTQK;

wherein the underlined portion corresponds to SEQ ID NO: 1.

Results

Identification of Compound 1 Through Encoded Library Technology Screening, Structure Guided Drug Design and Cellular Profiling.

Z $\alpha_1$-antitrypsin is a conformationally dynamic molecule that polymerises from a near-native conformation late in the folding pathway and therefore represents a non-classical target for drug discovery. Thus it was reasoned that hit finding may benefit from exploration of broad and minimally biased chemical space. An Encoded Library Technology (ELT) screen was used to search for binders to Z $\alpha_1$-antitrypsin. Glycosylated Z $\alpha_1$-antitrypsin, purified from the plasma of Z $\alpha_1$-antitrypsin homozygotes, was used since this represents the disease-relevant human pathophysiological drug target. ELT selections were performed by immobilising Z $\alpha_1$-antitrypsin on an antibody-based affinity resin for incubation with DNA-encoded compound libraries, with secondary screening by thermal shift experiments.

A single lead series of chiral hydroxy-carboxamides was identified from the ELT screen that demonstrated functional activity at blocking polymerisation in the TR-FRET immunoassay. Optimisation of the initial hit followed a structure-based design approach, exploiting knowledge from crystal structures of small molecule ligands complexed with $\alpha_1$-antitrypsin. The central hydroxy carboxamide was found to facilitate binding to Z $\alpha_1$-antitrypsin. An alkyl side chain (at the carbon adjacent to the N atom of the carboxamide) was also found to be beneficial, particularly a propyl side chain. Medicinal chemistry development focused on modifications such as the aromatic groups at the terminal ends of the compound. This resulted in the discovery of Compound 1.

Compound 1 is a Potent Inhibitor of Polymerisation In Vitro and in Cell Models of Disease Compound 1 binds to Z $\alpha_1$-antitrypsin with a high affinity ($K_D$) of 1.5 nM as determined by a competition binding assay with a fluorescently labelled derivative; a similar value was obtained by microscale thermophoresis. The binding demonstrates selectivity with at least 50-fold lower affinity for plasma-purified wild-type M $\alpha_1$-antitrypsin.

The shape of the curves and native mass spectrometry were consistent with a single compound binding site. No binding of the fluorescent derivative to polymers of the Z variant could be observed, indicating loss of the binding pocket upon polymerisation and a resulting marked conformational selectivity. The rate of interaction of the compound with the target could be monitored through changes in intrinsic tryptophan fluorescence; this property was used to determine the second-order association rates for Compound 1 binding to Z ($4.1 \times 10^4$ $M^{-1}$ $s^{-1}$) and M $\alpha_1$-antitrypsin ($2.1 \times 10^2$ $M^{-1}$ $s^{-1}$). From these values, first-order dissociation rates were calculated for Z ($6.1 \times 10^{-5}$ $s^{-1}$) and M $\alpha_1$-antitrypsin ($1.6 \times 10^{-5}$ $s^{-1}$) and found to be of the same order of magnitude. Therefore, the selectivity of the compound for Z over M $\alpha_1$-antitrypsin is dominated by the difference in the rate of association rather than dissociation.

Compound 1 was found to ablate polymerisation in vitro of plasma-derived Z $\alpha_1$-antitrypsin in a dose-dependent manner with a measured pIC50 of 8.3, near the tight binding limit of the TR-FRET assay. Its ability to block Z $\alpha_1$-antitrypsin polymerisation in the ER during folding was assessed by adding Compound 1 to CHO-TET-ON-Z-A1AT cells (Ordóñez et al. Hepatology. 2013; 57(5):2049-60) with simultaneous induction of Z $\alpha_1$-antitrypsin expression using doxycycline. In comparison with controls, Compound 1 completely blocked the intracellular formation of Z $\alpha_1$-antitrypsin polymers, as measured by staining with the 2C1 anti-$\alpha_1$-antitrypsin polymer monoclonal antibody (pIC50=6.3). To investigate whether in addition to blocking polymerisation, Compound 1 was also able to increase secretion of Z $\alpha_1$-antitrypsin, Z $\alpha_1$-antitrypsin expression was induced in CHO-TET-ON-Z-A1AT cells, Compound 1 was added, and the total Z $\alpha_1$-antitrypsin in the supernatant was measured by immunoassay after 6 hours. Compound 1 increased secreted levels approximately 3-fold compared to vehicle control with a pEC50 of 6.3. Similar potency between the effects on secretion and polymerisation was observed for other compounds of the invention, supporting the hypothesis that these effects are caused by the same pharmacological mode of action.

In order to confirm that the potency and efficacy of Compound 1 in CHO-TET-ON-Z-A1AT was a reasonable estimate of what could be expected in hepatocytes with endogenous levels of expression, the effect of Compound 1 on the secretion and polymerisation of Z $\alpha_1$-antitrypsin was measured in iPSC-derived hepatocytes with the ZZ $\alpha_1$-antitrypsin genotype (Yusa et al. Nature. 2011; 478:391-4). Compound 1 inhibited polymerisation and increased secretion with a similar potency in iPSC-hepatocytes as in CHO-TET-ON-Z-A1AT cells, with a pIC50 of 6.4 and pEC50 of 6.5 respectively, and with a similar efficacy, inducing an approximately 3-fold increase of secreted levels of Z $\alpha_1$-antitrypsin.

Since all individuals with the $\alpha_1$-antitrypsin Z allele exhibit polymer in their livers but only a relatively small fraction develop clinical liver disease it is likely $\alpha_1$-antitrypsin liver disease in adults is a two-hit process whereby the generation of Z $\alpha_1$-antitrypsin polymer in the liver sensitises the liver to a secondary insult such as alcohol, drug or liver fat. To investigate the ability of Compound 1 to protect cells from sensitisation to a secondary toxin, Z $\alpha_1$-antitrypsin expression was induced in CHO-TET-ON-Z-A1AT cells in the presence or absence of 10 μM Compound 1 before exposure to varying concentrations of the ER stressor tunicamycin. In a cell viability assay, cells expressing wild-type M $\alpha_1$-antitrypsin were less sensitive to tunicamycin than cells expressing Z $\alpha_1$-antitrypsin. Compound 1 completely abrogated polymer formation in Z $\alpha_1$-antitrypsin expressing cells and restored sensitivity of $\alpha_1$-antitrypsin expressing cells to that of the wild-type control cells.

Compound 1 Binds to a Novel Cryptic Binding Site More Frequently Sampled by the Z Variant High resolution crystal structures of $\alpha_1$-antitrypsin complexed with Compound 1 were generated by soaking compound into apo $\alpha_1$-antitrypsin crystals (Table 1).

TABLE 1

Data collection and refinement statistics
Compound 1

| Data collection | |
| --- | --- |
| Space group | C2 |
| Cell dimensions | |
| a, b, c (Å) | 113.9, 39.6, 90.5 |
| α, β, γ (°) | 90.0, 105.0, 90.0 |
| Resolution (Å) | 55.05-1.76 (1.85-1.76) |
| $R_{merge}$ (%) | 0.025 (0.398) |
| CC-half | 0.999 (0.842) |
| I/σI | 19.6 (2.4) |
| Completeness (%) | 99.2 (99.2) |
| Multiplicity | 3.3 (3.3) |
| Refinement | |
| Resolution (Å) | 55.05-1.76 (1.80-1.76)* |
| No. reflections | 36959 (2858) |
| $R_{work}/R_{free}$ | 18.7 (27.8)/22.2 (32.1) |
| No. atoms | |
| Protein | 2868 |
| Water | 289 |
| B-factors | |
| Protein | 46.8 |
| Water | 59.2 |

TABLE 1-continued

Data collection and refinement statistics
Compound 1

| R.m.s. deviations | |
| --- | --- |
| Bond lengths (Å) | 0.05 |
| Bond angles (°) | 1.03 |

*Values in parentheses are for highest-resolution shell.

The structures reveal that interaction with the compounds induces the formation of a cryptic binding site not evident in apo structures, at the top of β-sheet-A behind strand 5. This region is referred to as the 'breach' as it is the point at which the reactive centre loop first inserts during protease inhibition (Whisstock et al. J Mol Biol. 2000; 295(3):651-65), and includes the site of the E342K Z-mutation.

Figure 2:
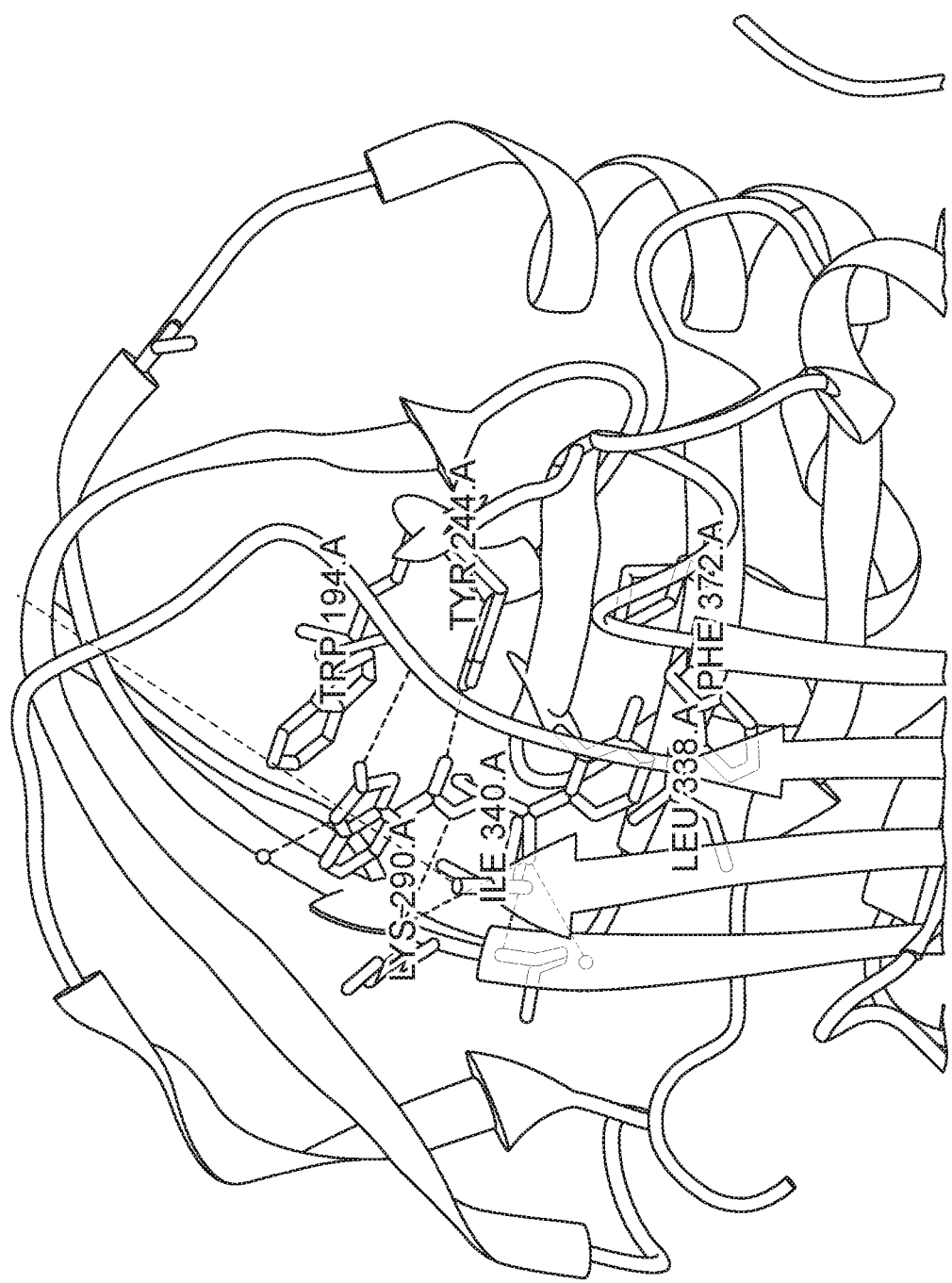
FIG. 2 is a representative image of a portion of the crystallised complex formed between a representative compound of the present invention and an $\alpha_1$-antitrypsin protein, as described in more detail in Example 2 (specifically the portion contains the binding site between the protein and the compound of the invention).
Figure 3:
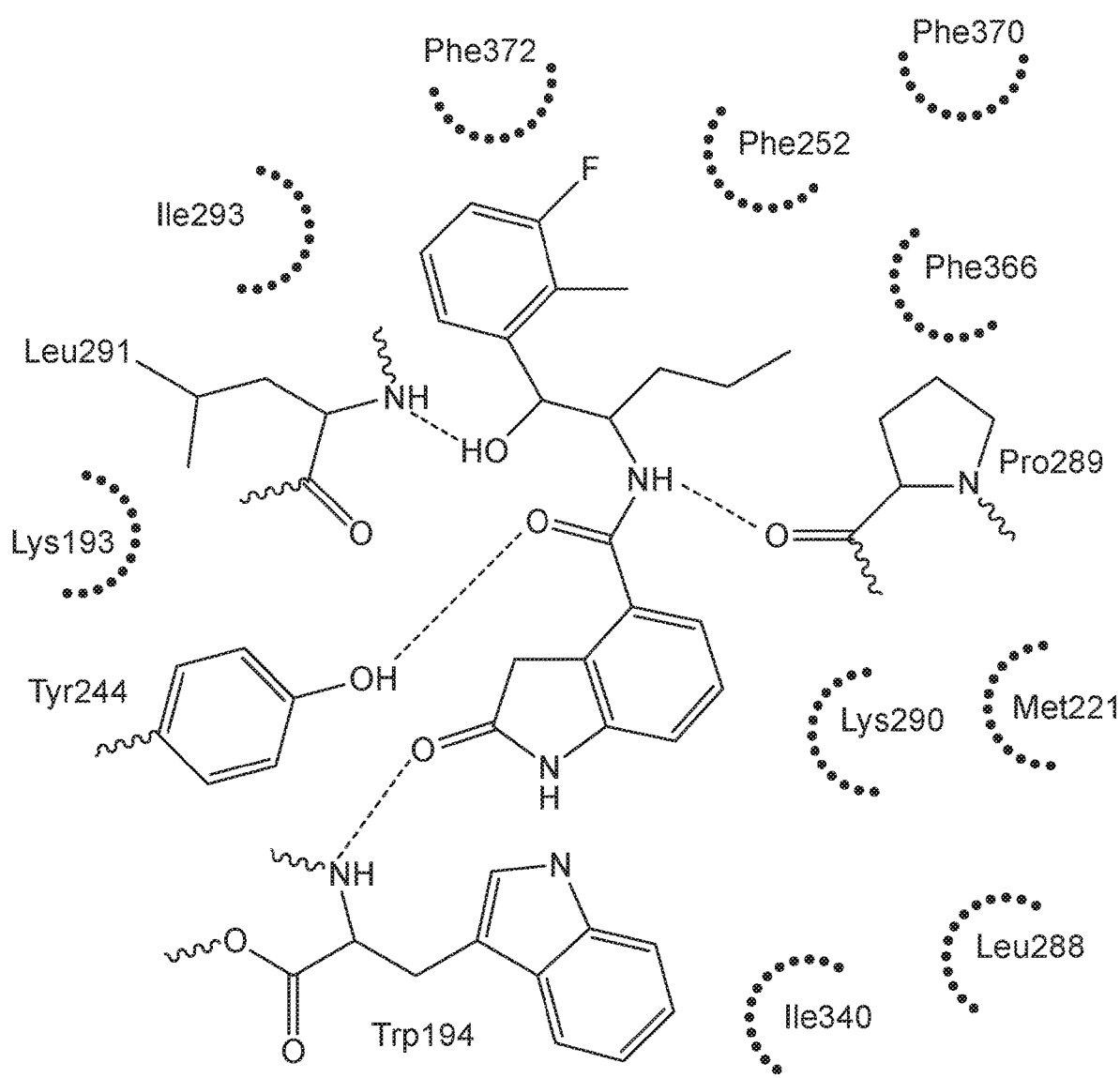
FIG. 3 is a schematic, two-dimension visualisation of a representative compound of the present invention at the binding site of the protein, and highlighting some of the amino acid residues that comprise the binding site as well as partial chemical structures within the protein that form significant intermolecular interactions (e.g., hydrogen bonds) to the compound (shown as broken lines), as described in more detail in Example 2.

Representative images of the identified binding site are shown in FIGS. 1 to 3. FIG. 1 shows an overview of the protein bound to Compound 1 (residues 342-356 are disordered and hence missing from the representation). FIG. 2 provides a more detailed view of the binding site including some of the proximate residues, with hydrogen bonds shown as broken lines. FIG. 3 is a schematic, two-dimension visualisation of Compound 1 at the binding site of the protein, and highlighting some of the amino acid residues that comprise the binding site as well as partial chemical structures within the protein that form significant intermolecular interactions (e.g., hydrogen bonds) to Compound 1 (shown as broken lines).

In more detail, the structure of $\alpha_1$-antitrypsin complexed with Compound 1 reveals that the oxindolyl ring stacks with the side chain of Trp194 whilst the carbonyl group forms a hydrogen bond with Trp194 mainchain (see FIG. 2 and FIG. 3), consistent with the change in intrinsic tryptophan fluorescence induced by binding. The phenyl ring and the propyl chain occupy two highly hydrophobic pockets. Hydrogen bonds are formed between the Compound 1 hydroxyl group and the Leu291 backbone, the amide nitrogen hydrogen and the backbone carbonyl oxygen of Pro289, and between the amide carbonyl and the Tyr244 hydroxyl group (see FIG. 2 and FIG. 3). As a consequence, there is displacement of residues 189 to 195, 290 to 295 and 336 to 342, of strand 5A with a corresponding loss of electron density for the proximal hinge of the reactive centre loop, an ~170° rotation of the Trp194 side-chain and 3.8 Å shift in the Tyr244 hydroxyl group and displacement of residues 196-203. A comparison of the Compound 1-bound structure with the apo form shows an overall 0.64 Å root-mean-square deviation for 335 residue pairs.

Specifically, therefore, Compound 1 was found to be capable of binding to the $\alpha_1$-antitrypsin at a cryptic binding site as defined elsewhere herein. For completeness, it is noted that the hexahistidine affinity tag and amino acids provided by the expression vector in the protein used were not apparent in the electron density profile of the binding site and were not therefore associated with the binding of compound 1. Similarly, the mutated Ser232 (replacing Cys232 in the wild-type protein) was not at a position directly associated with the compound binding site.

Compound 1 Interferes with the Transition to the Polymerisation-Prone Intermediate M* by Stabilising β-Sheet A Polymerisation of $\alpha_1$-antitrypsin occurs from a transient intermediate state known as M*, that is readily populated by the Z variant. One of the hallmarks of M* is its recognition by environment-sensitive fluorescent reporter dyes. Thermal shift assays that make use of the dye SYPRO Orange report the stability of the protein native state against heat-induced unfolding. A series of experiments, performed using different temperature gradients in the presence and absence of 50 M Compound 1, demonstrated a marked increase in the transition midpoint temperature; in $\alpha_1$-antitrypsin this is indicative of a native state stabilised against the transition to M*. Correspondingly, in a constant-temperature experiment, oligomers were generated at higher temperatures in the presence of the compound than in its absence when visualised by non-denaturing PAGE. Native state stability can also be probed by equilibrium unfolding using chemical denaturants, where a peak in bis-ANS fluorescence corresponds with a maximally populated unfolding intermediate. The measured profiles showed that for guanidinium hydrochloride-induced unfolding this point occurs at 1.8 M denaturant in the presence of 50 μM Compound 1, reflecting an increase in native state stability with respect to its absence (1.2 M).

Mutations that interfere with the opening of β-sheet A or that perturb its interaction with the N-terminal portion of the reactive centre loop alter the ability of serpins to inhibit target proteases. The stoichiometry of inhibition (SI) was determined for M and Z $\alpha_1$-antitrypsin in discontinuous experiments against a model target protease, chymotrypsin. The pre-incubation of both variants with Compound 1 led to a >98% loss of protease inhibitory activity. Resolution of the products of the interaction by SDS-PAGE showed full cleavage of the reactive centre loop; therefore, this is not a consequence of the protease recognition site in the reactive centre loop becoming inaccessible to the enzyme. These data are consistent with a mechanism in which the compound stabilises β-sheet A against conformational change that mediates both inhibitory activity and pathological misfolding. To investigate whether this activity was consistent with action as a chemical chaperone, M and Z $\alpha_1$-antitrypsin were unfolded in vitro into 6 M guanidine hydrochloride, and rapidly refolded by snap dilution into denaturant-free buffer in the presence or absence of Compound 1. Electrophoresis of the products by non-denaturing PAGE showed an anodally-shifted migration for the Z variant in the absence of compound—consistent with a misfolded byproduct of M* (Ekeowa et al. Proc Natl Acad Sci USA. 2010; 107(40): 17146-51)—which was corrected at stoichiometric concentrations and above.

Characterisation of Drug-Like Properties of Compound 1

In order to investigate suitability of Compound 1 for progression into in vivo studies and the potential for taking forward as a clinical candidate for testing in human, Compound 1 was profiled against a panel of in vitro assays for off-targets considered predictive of potential safety liabilities. Compound 1 was inactive against the majority of these targets with a low level of activity close to the lower limit of sensitivity in 16 assays. The measured potency of these marginal activities were at least 10-fold below the cellular activity of Compound 1 at blocking Z $\alpha_1$-antitrypsin polymerisation (pEC50 6.3). Loss of inhibitory activity represents a means by which possible off-target engagement with other serpins can be evaluated. However in contrast to $\alpha_1$-antitrypsin upon incubation with 50 μM Compound 1 the inhibitory activity of the homologues antithrombin, neuroserpin and antichymotrypsin was not affected.

Since Compound 1 exhibited a good level of selectivity over the off-target panel and other serpins the in vitro and in vivo PK properties of the molecule were explored with a view to exploring target engagement in vivo. Compound 1 has a measured ChromLogD (pH7.4) of 3.8, low binding to human serum albumin of 84.2% and good solubility of amorphous drug substance in FaSSIF.

Compound 1 had in vitro ADME properties suitable for in vivo evaluation of the pre-clinical and clinical pharmacology of the molecule. Permeability was high and in vitro clearance in cryopreserved hepatocytes was low in human and dog (0.3±0.05 and <0.65 mL/min/g respectively) and moderate to high in mouse and rat (4.6 and 7.4±0.7 mL/min/kg respectively). Mean exposure of Compound 1 in blood in the male CD-1 mouse increased with dose following single PO administration at 10, 30 or 100 mg/kg (mean dose-normalised $C_{max}$ 58±112, 113±27 and 113±27; $DNAUC_{inf}$ 202±101, 294±47 and 403±246, respectively).

Compound 1 Increases Secretion of Z $\alpha_1$-Antitrypsin in a Transgenic Mouse Model of $\alpha_1$-Antitrypsin Deficiency In order to investigate the therapeutic potential of Compound 1 in Z $\alpha_1$-antitrypsin deficiency, the compound was tested in a transgenic mouse model engineered with a random insertion of the human Z $\alpha_1$-antitrypsin gene (Teckman et al. Am J Physiol Gastrointest Liver Physiol. 2004; 286:G851-G62). To determine a suitable dose regimen for Compound 1 in these studies the total and unbound exposure in transgenic mice was estimated in an in silico model. This was based on the observed PK parameters from wild-type mice and incorporating a circulating high affinity sink for drug, representing the mean 5 µM total Z $\alpha_1$-antitrypsin in the blood of the mice at baseline with an affinity for drug of 1.5 nM. Based on this modelling an oral dosing regimen of 100 mg/kg three times a day was predicted to maintain the free drug concentration above the EC50 measured for secretion of Z $\alpha_1$-antitrypsin (~300 nM) for the duration of the dosing period. In contrast, unbound concentrations of Compound 1 after 30 and 10 mg/kg three times a day would be expected to be well below the EC50 for secretion for most of the dosing period.

To explore the PK-PD relationship of Compound 1, Z $\alpha_1$-antitrypsin transgenic animals were dosed with 100, 30 or 10 mg/kg Compound 1 three times a day and on day 6 blood and liver were harvested at 3 hr (~$C_{max}$) and 8 hr ($C_{min}$) after the dose for the measurement of total and free drug in both tissues. Blood was also harvested for the measurement of monomeric Z $\alpha_1$-antitrypsin in plasma. Total concentrations of Compound 1 were determined by specific LC-MS/MS assay and the free unbound drug in both tissues was determined using equilibrium dialysis and used to derive unbound concentrations. Free and total blood concentrations were consistent with the predictions and confirmed that the $C_{min}$ levels of the free drug concentration was at or above 300 nM for the majority of the dosing period following 100 mg/kg dosing, whereas 30 mg/kg and 10 mg/kg doses resulted in free drug levels in blood significantly below the cellular EC50 concentrations for a large part of the dosing period. Both free and total drug concentrations of Compound 1 at the targeted site of action in the liver were equivalent to those in blood.

Recent work has shown that a significant fraction of the total Z $\alpha_1$-antitrypsin in the circulation is in the polymeric conformation (Tan et al. Eur Respir J. 2014; 43(5):1501-4). Since there are no antibodies specific for monomeric Z $\alpha_1$-antitrypsin to directly determine its concentration, a deconvolution method was developed based on immunoassays with antibodies for either total or polymeric $\alpha_1$-antitrypsin, and calibration curves with purified monomeric and polymeric Z $\alpha_1$-antitrypsin. Monomeric Z $\alpha_1$-antitrypsin was measured in plasma samples following 6 days of dosing and levels were normalised to each animals' pre-dose control levels to account for the natural variation of Z $\alpha_1$-antitrypsin between animals. 100 mg/kg Compound 1 resulted in a 6- to 7-fold increase in circulating monomeric Z $\alpha_1$-antitrypsin levels demonstrating robust target engagement in the liver. 30 mg/kg and 10 mg/kg groups also gave significant, dose-dependent increases in circulating Z $\alpha_1$-antitrypsin despite free concentrations being below the cellular EC50 for secretion for much or all of the dosing period. Total drug levels and changes in Z $\alpha_1$-antitrypsin following 3 days of dosing were indistinguishable to those following 6 days of dosing.

Taken together these results confirm target engagement in the liver following oral dosing of Compound 1 and demonstrate that circulating levels of Z $\alpha_1$-antitrypsin can be increased by a therapeutically relevant magnitude in a model $\alpha_1$-antitrypsin deficiency. The increase of circulating Z $\alpha_1$-antitrypsin at lower doses may suggest that achieving sustained free drug levels above the cellular EC50 for secretion may not be required in vivo to significantly increase Z $\alpha_1$-antitrypsin levels.

Since Compound 1 blocks polymer formation in cells the effect of dosing Compound 1 on liver polymer levels was explored. It has recently been shown that Z $\alpha_1$-antitrypsin polymers formed in CHO-TET-ON-Z-A1AT and ZZ-iPSC-hepatocytes are cleared from cells with a t½ of between 8 and 48 hours depending on whether they partition to the soluble or insoluble fractions. Since the compound does not bind Z $\alpha_1$-antitrypsin polymer, an effect on total liver polymer levels will be dependent on the rate at which the liver can clear the polymer already present and the rate at which polymer continues to accumulate in animals not treated with drug. Compound 1 was therefore dosed at 100 mg/kg three times a day as above for 20 days. On days 15 and 21 of dosing, changes of monomeric Z $\alpha_1$-antitrypsin plasma samples were determined as above, and increases of 7- to 8-fold over the pre-dosing baseline levels were observed, similar to the effect in animals dosed for 3 or 6 days, consistent with sustained target engagement through the dosing period. Liver polymer levels were investigated by staining with 2C1 anti-polymer monoclonal antibody and were scored blinded either by a pathologist or by quantification using an algorithm to measure all areas of positive staining. There was no difference observed in total liver polymer load via manual or quantitative scoring. Aged Z $\alpha_1$-antitrypsin mice exhibit dense polymeric inclusions that are not observed in livers of individuals with $\alpha_1$-antitrypsin deficiency.

To investigate whether there is a subpopulation of polymer in the liver that was responding to compound over the time frame of the experiment, areas of staining were divided into low, medium and high intensity regions and scored separately for response to compound. No effect of compound was discernible in any of these subdivided regions. Given that polymer formation is completely blocked by Compound 1 in vitro it was concluded that longer term dosing will be required to affect total polymer burden in Z $\alpha_1$-antitrypsin transgenic mice. However, it remains to be determined whether the mouse liver has the capacity to clear Z $\alpha_1$-antitrypsin polymer following the chronic insult of generating Z $\alpha_1$-antitrypsin in the liver throughout life or indeed whether this is required to elicit a benefit to the sensitivity to secondary triggers of liver dysfunction.

Discussion

The co-crystal structures with $\alpha_1$-antitrypsin provide insight into the mode of action by which Compound 1 inhibits Z $\alpha_1$-antitrypsin polymerisation. Whilst the mechanism that results in pathological liver polymer formation has not been established, the obligate and central role of the reactive centre loop in this process is well-accepted (see (a) Lomas et al. Nature. 1992; 357:605-7; (b) Ekeowa et al. Proc Natl Acad Sci USA. 2010; 107(40):17146-5; and (c) Yamasaki et al. EMBO Rep. 2011; 12(10):1011-7). All extant models are based on the insertion of an extra β-strand derived from the reactive centre loop between strands 3 and 5 of the A-sheet, facilitated by the destabilising effect of the Z mutation on this structural element. The co-crystal structure of $\alpha_1$-antitrypsin and Compound 1 suggests that the compound may ameliorate the effect of the E342K Z-mutation due to: (i) optimisation of hydrophobic packing in the breach region; (ii) formation of hydrogen bonds with buried polar atoms; and also (iii) displacement of the backbone at the top of strand 5A into a configuration less compatible with partial loop insertion, which is suggested to be an early step in loop-sheet polymerisation (Gooptu et al. Proc Natl Acad Sci (USA). 2000; 97(1):67-72.) and an obligate one in C-terminal polymerisation (Yamasaki et al. EMBO Rep. 2011; 12(10):1011-7.). The displacement evident at the top of strand 5A is consistent with the association rate-driven preference for the Z variant, which destabilises this region with respect to the wild-type protein. In the crystal structures the side-chain at 342 is oriented towards the solvent, and does not directly interact with Compound 1; thus the key parameter driving compound preference is likely to be an increased availability of the cryptic pocket. The pocket, once formed, appears to be structurally equivalent in both variants as reflected by a similar rate of dissociation. This mode of action is also compatible with the lack of binding to polymers, in which partial or complete insertion of the reactive centre loop completes a beta-hairpin turn that would occlude the compound binding site.

Upon Compound 1 binding within the breach region, there is a marked stabilisation of the $\alpha_1$-antitrypsin native state against the conformational change associated with M* intermediate formation. This in turn prevents the formation of polymers. Precedent for this general mechanism can be found in a tool monoclonal antibody that exerted a similar effect on $\alpha_1$-antitrypsin (Ordóñez et al. FASEB J. 2015; 29:2667-78; Motamedi-Shad et al. Biochem J. 2016; 473 (19):3269-90).

The lack of serpin activity in the lower airways leading to digestion of the lung parenchyma by locally-released neutrophil elastase contributes to the emphysema observed in individuals with $\alpha_1$-antitrypsin deficiency since rare patients who are completely null for $\alpha_1$-antitrypsin develop panlobular emphysema (Fregonese et al. Respir Med. 2008; 102(6):876-84.) and $\alpha_1$-antitrypsin replacement therapy has demonstrated some benefit on disease progression (Chapman et al. Lancet. 2015; 386(9991):360-8.). Compound 1 increases Z $\alpha_1$-antitrypsin secretion by correcting the folding defect and increases plasma concentrations of the serpin up to 8-fold in a transgenic mouse model of $\alpha_1$-antitrypsin deficiency Since Compound 1 inhibits the serpin activity of $\alpha_1$-antitrypsin whilst being bound to the protein it would not be expected to significantly increase serpin activity during the dosing period, indeed Compound 1 would inhibit the serpin activity of residual $\alpha_1$-antitrypsin in patients and would be expected to block activity of replacement therapy should this be co-administered with Compound 1. However, the half-life of monomeric Z $\alpha_1$-antitrypsin in human is believed to be ~3-5 days whereas drug would be expected to be cleared with a t½ of a few hours after dosing raising the possibility of a pulsatile dosing regimen that would lead to increased, active serpin. The definition of how long exposure to drug would be required to significantly elevate levels, to deplete the inflammatory polymer in the lungs and the washout period between doses to retain serpin activity requires further study. Similarly, the risk-benefit of blocking residual serpin activity during the dosing period will need to be assessed; however, the slow development of the lung disease in individuals with $\alpha_1$-antitrypsin deficiency over many decades suggests that acute effects associated with inhibition of serpin activity are unlikely. $\alpha_1$-antitrypsin polymers have been identified in the lungs of COPD patients with two normal $\alpha_1$-antitrypsin alleles, suggesting that $\alpha_1$-antitrypsin polymers may be a prevalent feature of the inflammation in COPD, independent of $\alpha_1$-antitrypsin genotype (Bazzan et al. Chest., 2018; 154:607-16).

Compound 1 blocks Z $\alpha_1$-antitrypsin polymerisation in cell free media and in the ER of cells and newly formed polymer is cleared by cells via secretion, proteasomal degradation or autophagy with a half-life of 8-48 hours. However, no reduction in Z $\alpha_1$-antitrypsin polymers was observed in the liver after 20 days of dosing Compound 1 in a Z $\alpha_1$-antitrypsin transgenic mouse despite a 7-fold increase in circulating levels within 3 days of dosing which was maintained throughout the experiment, indicating robust target engagement. The likely explanation for this is that the polymers that build up in the livers of the transgenic mice are not cleared as readily as those that can be generated in model systems such as CHO cells and iPSC-hepatocytes over a few days. Whilst this likely results from chronicity of insult, the molecular or cellular mechanism of this is unclear but cellular aging and senescence may be a contributor to this effect. Previous studies with the autophagy activator Carbamazepine have demonstrated pronounced effects on liver polymer in Z $\alpha_1$-antitrypsin transgenic mice following 2 weeks of dosing suggesting that the liver does retain the ability to clear polymer following chronic insult of Z $\alpha_1$-antitrypsin polymer accumulation (Hidvegi et al. Science. 2010; 329:229-32.). In contrast, RNAi approaches that inhibit Z $\alpha_1$-antitrypsin expression and polymer formation have reported decreases in Z $\alpha_1$-antitrypsin in transgenic mouse liver following 12-33 weeks of treatment, albeit without reports of data at earlier timepoints (Guo et al. J Clin Invest 2014; 124(1):251-61). Together these data suggest that the liver retains the ability to clear polymer following chronic insult and that it is likely that Compound 1 will need to be dosed to transgenic Z $\alpha_1$-antitrypsin mice for significantly longer than 20 days to demonstrate an effect on total liver polymer levels. It remains to be seen whether the built-up polymer is actually toxic to the cells and needs to be cleared from the liver in order to have some functional benefit or whether the accumulated polymer inclusions are actually inert and shutting off production of polymer is sufficient to restore the functioning of the ER and health of the cells (Ordóñez et al. Hepatology. 2013; 57(5):2049-60; Dickens et al. FASEB J. 2016; 30(12):4083-97).

The observed steady state total and free compound levels of Compound 1 in the transgenic Z $\alpha_1$-antitrypsin mouse were predicted well by the in silico PK model built on in vitro metabolic clearance data and plasma protein binding data, in vivo PK data from wild type mice and a term comprising a 5 µM circulating sink for drug with an affinity of 1.5 nM, representing the Z $\alpha_1$-antitrypsin within blood. The target free drug concentration has been selected based on the observed potency in the in vitro secretion assays in which the total drug approximates to the free drug in the assay. However, the increase in Z $\alpha_1$-antitrypsin in the circulation at the lower doses of Compound 1 is surprising given that systemic free drug levels are between the EC10-EC20 and EC20-EC30 for the duration of the dosing period for 10 and 30 mg/kg doses respectively. The reason for this is unclear however it is possible that the target engagement in vivo is greater than predicted from the potency in the in vitro cellular assays. Alternatively, it is possible that the first pass effect of drug reaching the liver immediately after absorption delivers some efficacy over that predicted from modelling the compound concentration at steady state levels. Together these data suggest potential upsides for the required compound exposure to deliver efficacy in the clinic.

Novel Mechanism for Treating a Conformational Disease

The compounds of the invention are believed to stabilise monomeric Z $\alpha_1$-antitrypsin by binding at the head of strand 5 of J-sheet A thereby negating the local effect of the Z mutation (Lomas et al. Biochemistry. 1993; 32:500-8). Specifically they displace strand 5 towards strand 3 and so 'correct' the local perturbation induced by a lysine residue at position 342. The binding site of Compound 1 has not been identified in previous crystal structures of $\alpha_1$-antitrypsin (Elliott et al. Protein Science. 2000; 9:1274-81.). However their effect on blocking the transition of fully folded Z $\alpha_1$-antitrypsin to polymerogenic intermediate, and their efficacy in cell and animal models of disease, suggests that they are acting on Z $\alpha_1$-antitrypsin in a near-native or native conformation. This implies that polymers form from a near-native or native conformation, rather than a more extended intermediate, and that the small molecules prevent the monomer linking to form a polymer. This small molecule correction of the Z mutation provides a novel strategy to treat the liver disease in individuals with $\alpha_1$-antitrypsin deficiency.

What is claimed is:

1. A compound of formula (I)

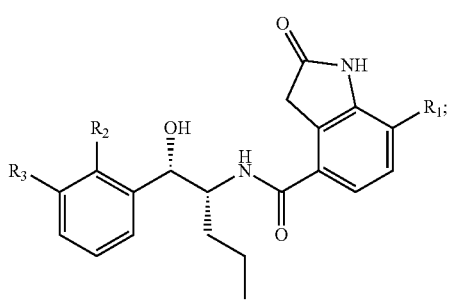

or a pharmaceutically acceptable salt thereof, wherein:

$R_1$ is selected from the group consisting of H, F, $CH_3$, $CH_2CH_3$, $CH_2CH_2CH_3$, $CH(CH_3)_2$, $NH_2$, $NHCH_3$, $N(CH_3)_2$, OH, Cl, Br and I;

$R_2$ is selected from the group consisting of $CH_3$, Cl, $CH_2CH_3$, $CH_2CH_2CH_3$, $CH(CH_3)_2$, $NH_2$, $NHCH_3$, $N(CH_3)_2$, OH, SH, CN, F, Br and I; and $R_3$ is selected from the group consisting of F, Cl, CN, $CH_3$, $CH_2CH_3$, $CH_2CH_2CH_3$, $CH(CH_3)_2$, $NH_2$, $NHCH_3$, $N(CH_3)_2$, OH, Br, I and SH.

2. The compound or pharmaceutically acceptable salt of claim 1, wherein $R_1$ is selected from the group consisting of H, F, $CH_3$, $NH_2$, OH and Cl;

$R_2$ is selected from the group consisting of $CH_3$, Cl, $NH_2$, OH, SH, CN and F; and $R_3$ is selected from the group consisting of F, Cl, CN, $CH_3$, $NH_2$, OH and SH.

3. The compound or pharmaceutically acceptable salt of claim 2, wherein $R_1$ is H, $R_2$ is $CH_3$ and $R_3$ is F;
$R_1$ is H, $R_2$ is $CH_3$ and $R_3$ is Cl;
$R_1$ is F, $R_2$ is Cl and $R_3$ is CN; or
$R_1$ is F, $R_2$ is Cl and $R_3$ is F.

4. A method for treating a disease or condition mediated by a Z-$\alpha_1$-antitrypsin mutation in a patient, the method comprising administering to the patient a therapeutically effective amount of the compound or pharmaceutically acceptable salt according to claim 1.

5. The compound or pharmaceutically acceptable salt of claim 1, wherein $R_1$ is H, $R_2$ is $CH_3$ and $R_3$ is F.

6. The compound or pharmaceutically acceptable salt of claim 1, wherein $R_1$ is H, $R_2$ is $CH_3$ and $R_3$ is Cl.

7. The compound or pharmaceutically acceptable salt of claim 1, wherein $R_1$ is F, $R_2$ is Cl and $R_3$ is CN.

8. The compound or pharmaceutically acceptable salt of claim 1, wherein $R_1$ is F, $R_2$ is Cl and $R_3$ is F.

9. The compound or pharmaceutically acceptable salt of claim 1, wherein:

$R_1$ is selected from the group consisting of H and F;
$R_2$ is selected from the group consisting of $CH_3$ and Cl; and
$R_3$ is selected from the group consisting of F, Cl and CN.

10. The method of claim 4, wherein the disease or condition mediated by the Z-$\alpha$1-antitrypsin mutation is $\alpha$1-antitrypsin deficiency, liver dysfunction, fibrosis, cirrhosis, liver failure, hepatocellular carcinoma, chronic obstructive pulmonary disease (COPD), asthma, emphysema, lung cancer, dermatitis, or pruritus.

11. The method of claim 4, wherein the disease or condition mediated by the α1-antitrypsin mutation is a respiratory disease and the method further comprises administering to the subject in need thereof a bronchodilator.

12. The method of claim 4, wherein the patient is human.

13. A method for treating a disease or condition mediated by a Z-α$_1$-antitrypsin mutation in a patient, the method comprising administering to the patient a therapeutically effective amount of the compound or pharmaceutically acceptable salt according to claim 8.

14. The method of claim 13, wherein the disease or condition mediated by the α1-antitrypsin mutation is α1-antitrypsin deficiency, liver dysfunction, fibrosis, cirrhosis, liver failure, hepatocellular carcinoma, chronic obstructive pulmonary disease (COPD), asthma, α1-antitrypsin, emphysema, lung cancer, dermatitis, or pruritus.

15. The method of claim 13, wherein the disease or condition mediated by the α1-antitrypsin mutation is a respiratory disease and the method further comprises administering to the subject in need thereof a bronchodilator.

16. The method of claim 13, wherein the patient is human.

17. A pharmaceutical composition comprising the compound or pharmaceutically acceptable salt of claim 1 and a pharmaceutically acceptable excipient.

18. A pharmaceutical composition comprising the compound or pharmaceutically acceptable salt of claim 8 and a pharmaceutically acceptable excipient.

19. A compound:

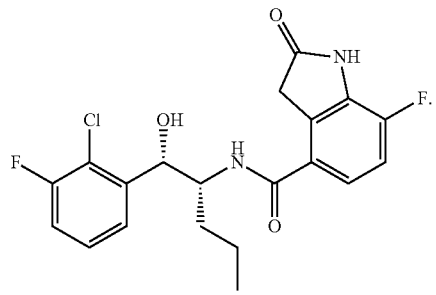 [SMILES: CCC[C@@H](NC(=O)c1ccc(F)c2c1CC(=O)N2)[C@@H](O)c1cccc(F)c1Cl]

20. A method for treating a disease or condition mediated by a Z-α$_1$-antitrypsin mutation in a patient, the method comprising administering to the patient a therapeutically effective amount of the compound according to claim 19.

21. The method of claim 20, wherein the disease or condition mediated by the Z-α1-antitrypsin mutation is α1-antitrypsin deficiency, liver dysfunction, fibrosis, cirrhosis, liver failure, hepatocellular carcinoma, chronic obstructive pulmonary disease (COPD), asthma, emphysema, lung cancer, dermatitis, or pruritus.

22. The method of claim 20, wherein the disease or condition mediated by the α1-antitrypsin mutation is a respiratory disease and the method further comprises administering to the subject in need thereof a bronchodilator.

23. The method of claim 20, wherein the patient is human.

* * * * *

SEQUENCE LISTING

```
<160> NUMBER OF SEQ ID NOS: 6

<210> SEQ ID NO 1
<211> LENGTH: 394
<212> TYPE: PRT
<213> ORGANISM: Artificial Sequence
<220> FEATURE:
<223> OTHER INFORMATION: alpha1-antitrypsin
<220> FEATURE:
<221> NAME/KEY: MISC_FEATURE
<222> LOCATION: (1)..(1)
<223> OTHER INFORMATION: Xaa is T or E
<220> FEATURE:
<221> NAME/KEY: MISC_FEATURE
<222> LOCATION: (101)..(101)
<223> OTHER INFORMATION: Xaa is R or H
<220> FEATURE:
<221> NAME/KEY: MISC_FEATURE
<222> LOCATION: (213)..(213)
<223> OTHER INFORMATION: Xaa is A or V
<220> FEATURE:
<221> NAME/KEY: MISC_FEATURE
<222> LOCATION: (232)..(232)
<223> OTHER INFORMATION: Xaa is C or S
<220> FEATURE:
<221> NAME/KEY: MISC_FEATURE
<222> LOCATION: (342)..(342)
<223> OTHER INFORMATION: Xaa is E or K
<220> FEATURE:
<221> NAME/KEY: MISC_FEATURE
<222> LOCATION: (376)..(376)
<223> OTHER INFORMATION: Xaa is D or E

<400> SEQUENCE: 1

Xaa Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
        50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Xaa Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125
```

Lys Phe Leu Glu Asp Val Lys Leu Tyr His Ser Glu Ala Phe Thr
        130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Xaa Thr Thr Val Lys Val Pro Met Met Lys Arg Leu
210                 215                 220

Gly Met Phe Asn Ile Gln His Xaa Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Xaa Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Xaa Gln Asn Thr Lys Ser Pro Leu Phe
    370                 375                 380

Met Gly Lys Val Val Asn Pro Thr Gln Lys
385                 390

<210> SEQ ID NO 2
<211> LENGTH: 418
<212> TYPE: PRT
<213> ORGANISM: Homo sapiens

<400> SEQUENCE: 2

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro

```
            100                 105                 110
Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 3
<211> LENGTH: 418
<212> TYPE: PRT
<213> ORGANISM: Artificial Sequence
<220> FEATURE:
<223> OTHER INFORMATION: full sequence of Z-A1AT

<400> SEQUENCE: 3

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45
```

```
Lys Ile Thr Pro Asn Leu Ala Glu Phe Ala Phe Ser Leu Tyr Arg Gln
 50                  55                  60
Leu Ala His Gln Ser Asn Ser Thr Asn Ile Phe Ser Pro Val Ser
 65                  70                  75                  80
Ile Ala Thr Ala Phe Ala Met Leu Ser Leu Gly Thr Lys Ala Asp Thr
                 85                  90                  95
His Asp Glu Ile Leu Glu Gly Leu Asn Phe Asn Leu Thr Glu Ile Pro
            100                 105                 110
Glu Ala Gln Ile His Glu Gly Phe Gln Glu Leu Leu Arg Thr Leu Asn
        115                 120                 125
Gln Pro Asp Ser Gln Leu Gln Leu Thr Thr Gly Asn Gly Leu Phe Leu
    130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
Ala Lys Lys Gln Ile Asn Asp Tyr Val Glu Lys Gly Thr Gln Gly Lys
            180                 185                 190
Ile Val Asp Leu Val Lys Glu Leu Asp Arg Asp Thr Val Phe Ala Leu
        195                 200                 205
Val Asn Tyr Ile Phe Phe Lys Gly Lys Trp Glu Arg Pro Phe Glu Val
    210                 215                 220
Lys Asp Thr Glu Glu Glu Asp Phe His Val Asp Gln Ala Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
        275                 280                 285
Asn Glu Leu Thr His Asp Ile Ile Thr Lys Phe Leu Glu Asn Glu Asp
    290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Lys Lys Gly
        355                 360                 365
Thr Glu Ala Ala Gly Ala Met Phe Leu Glu Ala Ile Pro Met Ser Ile
    370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys

<210> SEQ ID NO 4
<211> LENGTH: 404
<212> TYPE: PRT
<213> ORGANISM: Artificial Sequence
<220> FEATURE:
<223> OTHER INFORMATION: SEQ ID NO: 1 comprising an affinity tag
```

<400> SEQUENCE: 4

Met Arg Gly Ser His His His His His His Thr Asp Pro Gln Gly Asp
1               5                   10                  15

Ala Ala Gln Lys Thr Asp Thr Ser His His Asp Gln Asp His Pro Thr
            20                  25                  30

Phe Asn Lys Ile Thr Pro Asn Leu Ala Glu Phe Ala Phe Ser Leu Tyr
            35                  40                  45

Arg Gln Leu Ala His Gln Ser Asn Ser Thr Asn Ile Phe Phe Ser Pro
        50                  55                  60

Val Ser Ile Ala Thr Ala Phe Ala Met Leu Ser Leu Gly Thr Lys Ala
65                  70                  75                  80

Asp Thr His Asp Glu Ile Leu Glu Gly Leu Asn Phe Asn Leu Thr Glu
                85                  90                  95

Ile Pro Glu Ala Gln Ile His Glu Gly Phe Gln Glu Leu Leu Arg Thr
            100                 105                 110

Leu Asn Gln Pro Asp Ser Gln Leu Gln Leu Thr Thr Gly Asn Gly Leu
        115                 120                 125

Phe Leu Ser Glu Gly Leu Lys Leu Val Asp Lys Phe Leu Glu Asp Val
130                 135                 140

Lys Lys Leu Tyr His Ser Glu Ala Phe Thr Val Asn Phe Gly Asp Thr
145                 150                 155                 160

Glu Glu Ala Lys Lys Gln Ile Asn Asp Tyr Val Glu Lys Gly Thr Gln
                165                 170                 175

Gly Lys Ile Val Asp Leu Val Lys Glu Leu Asp Arg Asp Thr Val Phe
            180                 185                 190

Ala Leu Val Asn Tyr Ile Phe Phe Lys Gly Lys Trp Glu Arg Pro Phe
        195                 200                 205

Glu Val Lys Asp Thr Glu Glu Glu Asp Phe His Val Asp Gln Val Thr
210                 215                 220

Thr Val Lys Val Pro Met Met Lys Arg Leu Gly Met Phe Asn Ile Gln
225                 230                 235                 240

His Ser Lys Lys Leu Ser Ser Trp Val Leu Leu Met Lys Tyr Leu Gly
                245                 250                 255

Asn Ala Thr Ala Ile Phe Phe Leu Pro Asp Glu Gly Lys Leu Gln His
            260                 265                 270

Leu Glu Asn Glu Leu Thr His Asp Ile Ile Thr Lys Phe Leu Glu Asn
        275                 280                 285

Glu Asp Arg Arg Ser Ala Ser Leu His Leu Pro Lys Leu Ser Ile Thr
290                 295                 300

Gly Thr Tyr Asp Leu Lys Ser Val Leu Gly Gln Leu Gly Ile Thr Lys
305                 310                 315                 320

Val Phe Ser Asn Gly Ala Asp Leu Ser Gly Val Thr Glu Glu Ala Pro
                325                 330                 335

Leu Lys Leu Ser Lys Ala Val His Lys Ala Val Leu Thr Ile Asp Glu
            340                 345                 350

Lys Gly Thr Glu Ala Ala Gly Ala Met Phe Leu Glu Ala Ile Pro Met
        355                 360                 365

```
Ser Ile Pro Pro Glu Val Lys Phe Asn Lys Pro Phe Val Phe Leu Met
    370                 375                 380

Ile Glu Gln Asn Thr Lys Ser Pro Leu Phe Met Gly Lys Val Val Asn
385                 390                 395                 400

Pro Thr Gln Lys

<210> SEQ ID NO 5
<211> LENGTH: 24
<212> TYPE: PRT
<213> ORGANISM: Artificial Sequence
<220> FEATURE:
<223> OTHER INFORMATION: Signal peptide

<400> SEQUENCE: 5

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 6
<211> LENGTH: 11
<212> TYPE: PRT
<213> ORGANISM: Artificial Sequence
<220> FEATURE:
<223> OTHER INFORMATION: hexahistidine affinity tag and expression
      vector amino acids

<400> SEQUENCE: 6

Met Arg Gly Ser His His His His His His Thr
1               5                   10
```

UNITED STATES PATENT AND TRADEMARK OFFICE
CERTIFICATE OF CORRECTION

PATENT NO. : 11,919,856 B2
APPLICATION NO. : 17/848156
DATED : March 5, 2024
INVENTOR(S) : Kate Smith et al.

It is certified that error appears in the above-identified patent and that said Letters Patent is hereby corrected as shown below:

In the Claims

In Column 69, Line 7, Claim 11, replace "subject in need thereof" with --patient--;

In Column 69, Line 23, Claim 15, replace "subject in need thereof" with --patient--;

In Column 70, Line 28, Claim 22, replace "subject in need thereof" with --patient--.

Signed and Sealed this
Fourth Day of June, 2024

Katherine Kelly Vidal
*Director of the United States Patent and Trademark Office*